(12) United States Patent
Chiarle et al.

(10) Patent No.: US 8,980,287 B2
(45) Date of Patent: Mar. 17, 2015

(54) ANAPLASTIC LYMPHOMA KINASE (ALK) AS ONCOANTIGEN FOR LYMPHOMA VACCINATION

(75) Inventors: Roberto Chiarle, Savigliano (IT); Giorgio Inghirami, Castelnuovo Don Bosco (IT); Guido Forni, Turin (IT)

(73) Assignees: Roberto Chiarle, Savigliano (Cuneo) (IT); Giorgio Inghirami, Castelnuovo Don Bosco (Asti) (IT)

( * ) Notice: Subject to any disclaimer, the term of this patent is extended or adjusted under 35 U.S.C. 154(b) by 1055 days.

(21) Appl. No.: 12/237,787

(22) Filed: Sep. 25, 2008

(65) Prior Publication Data
US 2009/0118216 A1 May 7, 2009

Related U.S. Application Data

(60) Provisional application No. 60/960,414, filed on Sep. 28, 2007.

(51) Int. Cl.
  *A61K 31/00* (2006.01)
  *A61K 38/00* (2006.01)
  *A61K 31/704* (2006.01)
  *A61K 39/00* (2006.01)

(52) U.S. Cl.
  CPC ........... *A61K 31/704* (2013.01); *A61K 39/0011* (2013.01); *A61K 2039/53* (2013.01); *A61K 2039/55522* (2013.01)
  USPC .................. 424/277.1; 424/184.1; 424/185.1; 514/1.1; 514/19.2

(58) Field of Classification Search
  CPC .... C12Q 1/6886; C12Q 1/6883; C12Q 1/485; A61K 2300/00; A61K 39/0011; A61K 38/00; A61K 49/0056; A61K 9/0019
  See application file for complete search history.

(56) References Cited

FOREIGN PATENT DOCUMENTS

WO WO 03/042243 5/2003

OTHER PUBLICATIONS

Lowe et al., J. Cell. Biochem., May 2006, 98:235-242.*
Shaw et al., Frontiers in Bioscience, Jan. 2006, 11:1189-1198.*
Evans et al., Q. J. Med 1999: 92: 299-307.*
Jaffe, Elaine S. The 2008 WHO Classification of Lymphomas: Implications for clinical Practice and Translational Research. Hematology, 2009. 523-531.*
Sasaki et al. A Novel ALK Secondary Mutation and EGFR Signaling Cause Resistance to ALK Kinase Inhibitor. Cancer Research, 2011. 71:6051-6060.*
Gilboa et al. (The Promise of Cancer Vaccines. Nature Reviews, 2004. 4:401-411).*
Kanduc, D. (2008). Immunogenicity in Peptide-Immunotherapy: from Self/Nonself to Similar/Dissimiliar Sequences. In A. B. Sigalov (Ed.), Multichain Immune Recognition Receptor Signaling: From Spatiotemporal Organization to Human Disease. Landes Bioscience and Springer Science+Business Media. pp. 198-207.*
Lamant et al, Expression of the ALK Tyrosine Kinase Gene in Neuroblastoma, American Journal of Pathology 156(5):1711-1721 (2000).
Chen et al, "Oncogenic mutations of ALK kinase in neuroblastoma", Nature 455:971-974 (2008).
Chiarle et al, "The anaplastic lymphoma kinase in the pathogenesis of cancer", Nature Reviews 8:11-23 (2008).
Dirks et al, "Expression and Functional Analysis of the Anaplastic Lymphoma Kinase (*ALK*) Gene in Tumor Cell Lines", Int. J. Cancer 100:49-56 (2002).
Du et al, "Proteomic profiling of proteins dysregulted in Chinese esophageal squamous cell carcinoma", J. Mol. Med. 85(8):863-875 (2007)—Abstract.
George et al, "Activating mutations in ALK provide a therapeutic target in neuroblastoma", Nature 455:975-978 (2008).
Griffin et al, "Recurrent Involvement of 2p23 in Inflammatory Myofibroblastic Tumors", Cancer Research 59:2776-2780 (1999).
Janoueix-Lerosey et al, "Somatic and germline activating mutations of the ALK kinase receptor in neuroblastoma", Nature 455:967-970 (2008).
Jazii et al, "Identification of squamous cell carcinoma associated proteins by proteomics and loss of beta tropomyosin expression in esophageal cancer", World Journal of Gastroenterology 12(44):7104-7112 (2006).
Soda et al, "Identification of the transforming *EML4-ALK* fusion gene in non-small-cell lung cancer", Nature 448:561-566 (2007).
Lawrence et al, "*TPM3-ALK* and *TPM4-ALK* Oncogenes in inflammatory Myofibroblastic Tumors", American Journal of Pathology 157(2):377-384 (2000).
Lin et al, "Exon Array Profiling Detects EML4-ALK Fusion in Breast, Colorectal, and Non-Small Cell Lung Cancers", Mol. Cancer Res. 7:1466-1476 (2009).
Mossé et al, "Identification of ALK as a major familial neuroblastoma predisposition gene", Nature 455:930-935 (2008).
Osajima-Hakomori et al, "Biological Role of Anaplastic Lymphoma Kinase in Neuroblastoma", American Journal of Pathology 167(2):213-222 (2005).
Perez-Pinera et al, "Anaplastic Lymphoma Kinase is Expressed in Different Subtypes of Human Breast Cancer", Biochem. Biophys. Res. Commun. 358(2):399-403 (2007).
Pillay et al, "ALK protein expression in rhabdomyosarcomas", Histopathology 41:461-467 (2002).

(Continued)

*Primary Examiner* — Maria Leavitt
*Assistant Examiner* — Kimberly A Aron
(74) *Attorney, Agent, or Firm* — Nixon & Vanderhye P.C.

(57) ABSTRACT

Use of intracytoplasmatic domain of Anaplastic Lymphoma Kinase (ALK) protein and/or a nucleic acid molecule encoding for the intracytoplasmatic domain of Anaplastic Lymphoma Kinase (ALK) protein, of any species, for the preparation of a medicament, preferably a vaccine, for the treatment and/or prevention of a tumor in a subject, preferably a lymphoma.

5 Claims, 14 Drawing Sheets

(56) References Cited

OTHER PUBLICATIONS

Powers et al, "Pleiotrophin Signaling throught Anaplastic Lymphoma Kinase Is Rate-limiting for Glioblastoma Growth", The Journal of Biological Chemistry 277(16):14153-14158 (2002).

Zamo et al, "Anaplastic lymphoma kinase (ALK) activates Stat3 and protects hematopoietic cells from cell death", Oncogene 21:1038-1047 (2002).

Duyster et al, "Translations involving anaplastic lymphoma kinase (ALK)", Oncogene 20:5623-5637 (2001).

European Search Report issued Feb. 26, 2009 in connection with corresponding EP App No. 08164900.6.

Pan, C.H., et al, *J Formos Med Assoc.*, vol. 98, No. 11, p. 722-729, (Nov. 1999), "Modulation of Immune Responses to DNA Vaccines by Codelivery of Cytokine Genes." XP009003637 ISSN: 0929-6646.

Williams, D.M., et al, *British Journal of Haematology*, vol. 117, No. 4, p. 812-820, (Jun. 2002), "Anaplastic large cell lymphoma in childhood: analysis of 72 patients treated on The United Kingdom Children's Cancer Study 1Group chemotherapy regimens." XP-002514869 ISSN: 0007-1048.

Coluccia, AML, et al, *Expert Opin. Ther. Targets*, vol. 9, No. 3, p. 515-532, (Jun. 2005) "Anaplastic lymphoma kinase and its signaling molecules as novel targets in lymphoma therapy." XP008101881 ISSN: 1472-8222.

Chiarle, R., et al, *Nature Medicine*, vol. 14, No. 6, p. 676-680, (Jun. 2008), "The anaplastic lymphoma kinase is an effective oncoantigen for lymphoma vaccination." XP-002514870 ISSN: 1078-8956.

Chiarle, R., et al, *Nature Reviews/Cancer*, vol. 8, No. 1, p. 11-23 (Jan. 2008) "The anaplastic lymphoma kinase in the pathogenesis of cancer." XO-002514871 ISSN: 1474-175X.

* cited by examiner

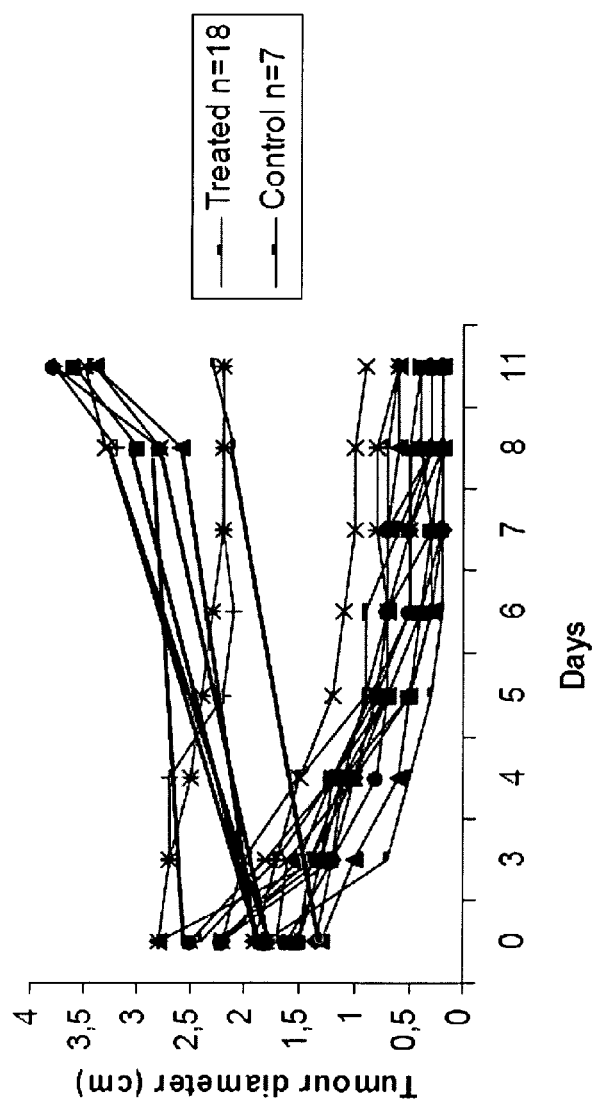
FIG. 2F
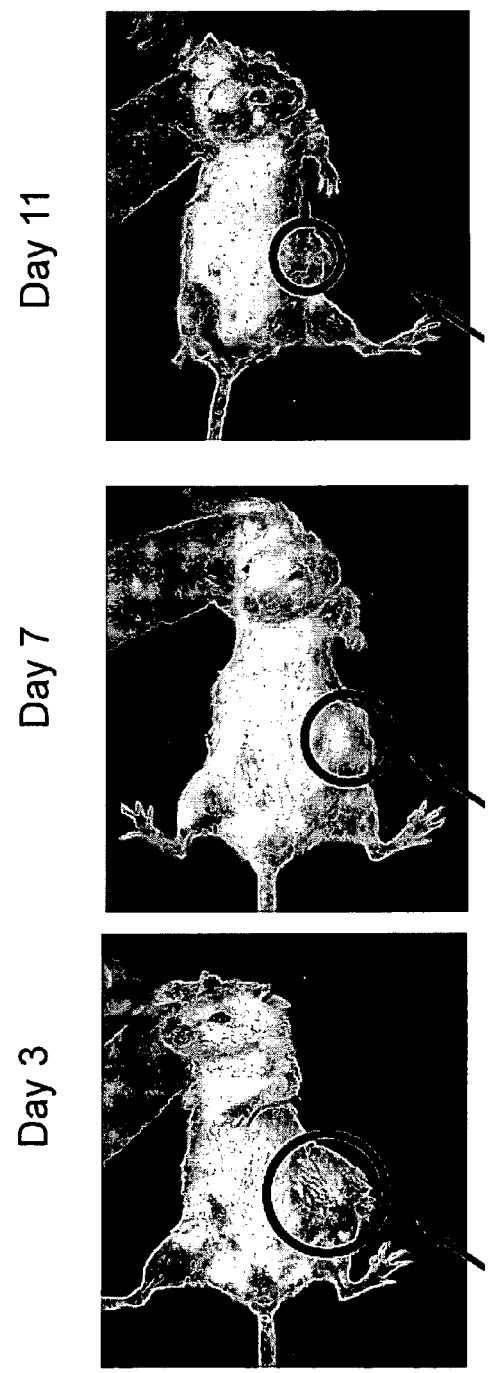

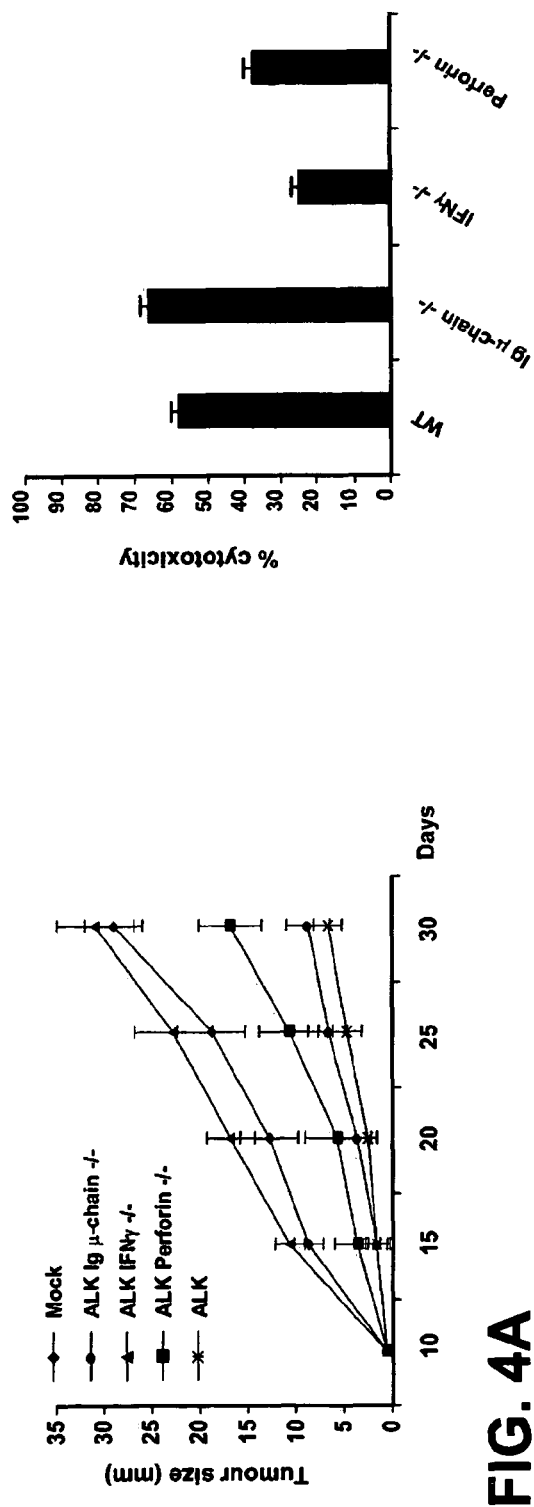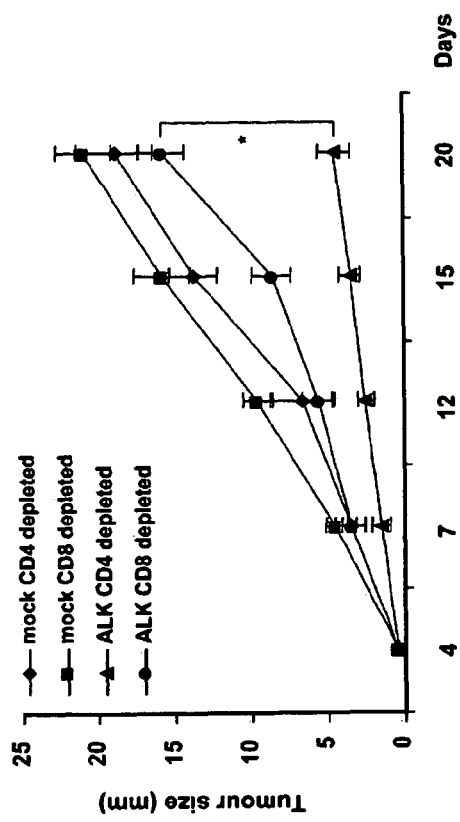
FIG. 4A
FIG. 4B
FIG. 4C

SEQUENCE LISTING

<160> NUMBER OF SEQ ID NOS: 7

<210> SEQ ID NO 1
<211> LENGTH: 1575
<212> TYPE: DNA

<213> ORGANISM: Artificial Sequence
<220> FEATURE:
<223> OTHER INFORMATION: cytoplasmic domain of ALK - human

<400> SEQUENCE: 1

```
tgctttgctg gcaagacctc ctccatcagt gacctgaagg aggtgccgcg gaaaaacatc      60
accctcattc ggggtctggg ccatggcgcc tttggggagg tgtatgaagg ccaggtgtcc     120
ggaatgccca acgacccaag cccccctgcaa gtggctgtga agacgctgcc tgaagtgtgc     180
tctgaacagg acgaactgga tttcctcatg gaagccctga tcatcagcaa attcaaccac     240
cagaacattg ttcgctgcat tggggtgagc ctgcaatccc tgccccggtt catcctgctg     300
gagctcatgg cggggggaga cctcaagtcc ttcctccgag acccgccc tcgcccgagc      360
cagccctcct ccctggccat gctggacctt ctgcacgtgg ctcgggacat tgcctgtggc     420
tgtcagtatt tggaggaaaa ccacttcatc caccgagaca ttgctgccag aaactgcctc     480
ttgacctgtc caggccctgg aagagtggcc aagattggag acttcgggat ggcccgagac     540
atctacaggg cgagctacta tagaaaggga ggctgtgcca tgctgccagt taagtggatg     600
cccccagagg ccttcatgga aggaatattc acttctaaaa cagacacatg gtcctttgga     660
gtgctgctat gggaaatctt ttctcttgga tatatgccat accccagcaa aagcaaccag     720
gaagttctgg agtttgtcac cagtggaggc cggatggacc cacccaagaa ctgccctggg     780
cctgtatacc ggataatgac tcagtgctgg caacatcagc ctgaagacag gcccaacttt     840
gccatcattt tggagaggat tgaatactgc acccaggacc cggatgtaat caacaccgct     900
ttgccgatag aatatggtcc acttgtggaa gaggaagaga agtgcctgt gaggcccaag     960
gaccctgagg gggttcctcc tctcctggtc tctcaacagg caaaacggga ggaggagcgc    1020
agcccagctg ccccaccacc tctgcctacc acctcctctg gcaaggctgc aaagaaaccc    1080
acagctgcag agatctctgt tcgagtccct agagggccgg ccgtggaagg gggacacgtg    1140
aatatggcat tctctcagtc caaccctcct tcggagttgc acaaggtcca cggatccaga    1200
aacaagccca ccagcttgtg gaacccaacg tacggctcct ggtttacaga gaaacccacc    1260
aaaaagaata tcctatagc aaagaaggag ccacacgaca ggggtaacct ggggctggag    1320
ggaagctgta ctgtcccacc taacgttgca actgggagac ttccgggggc ctcactgctc    1380
ctagagccct cttcgctgac tgccaatatg aaggaggtac ctctgttcag gctacgtcac    1440
ttcccttgtg ggaatgtcaa ttacggctac cagcaacagg gcttgccctt agaagccgct    1500
actgccctg gagctggtca ttacgaggat accattctga aaagcaagaa tagcatgaac    1560
cagcctgggc cctga                                                    1575
```

<210> SEQ ID NO 2
<211> LENGTH: 903
<212> TYPE: DNA
<213> ORGANISM: Artificial Sequence
<220> FEATURE:
<223> OTHER INFORMATION: portion of cytoplasmic domain of ALK - human

<400> SEQUENCE: 2

```
tgctttgctg gcaagacctc ctccatcagt gacctgaagg aggtgccgcg gaaaaacatc      60
accctcattc ggggtctggg ccatggcgcc tttggggagg tgtatgaagg ccaggtgtcc     120
ggaatgccca acgacccaag cccccctgcaa gtggctgtga agacgctgcc tgaagtgtgc     180
tctgaacagg acgaactgga tttcctcatg gaagccctga tcatcagcaa attcaaccac     240
cagaacattg ttcgctgcat tggggtgagc ctgcaatccc tgccccggtt catcctgctg     300
```

```
gagctcatgg cgggggggaga cctcaagtcc ttcctccgag agacccgccc tcgcccgagc    360
cagccctcct ccctggccat gctggacctt ctgcacgtgg ctcgggacat tgcctgtggc    420
tgtcagtatt tggaggaaaa ccacttcatc caccgagaca ttgctgccag aaactgcctc    480
ttgacctgtc caggccctgg aagagtggcc aagattggac ttcgggat ggcccgagac      540 atctacaggg cgagctacta tagaaaggga ggctgtgcca tgctgccagt taagtggatg    600
cccccagagg ccttcatgga aggaatattc acttctaaaa cagacacatg gtcctttgga    660
gtgctgctat gggaaatctt ttctcttgga tatatgccat accccagcaa aagcaaccag    720
gaagttctgg agtttgtcac cagtggaggc cggatggacc cacccaagaa ctgccctggg    780
cctgtatacc ggataatgac tcagtgctgg caacatcagc tgaagacag gcccaacttt     840 gccatcattt tggagaggat tgaatactgc acccaggacc cggatgtaat caacaccgct    900
ttg    903

<210> SEQ ID NO 3
<211> LENGTH: 1692
<212> TYPE: DNA
<213> ORGANISM: Artificial Sequence
<220> FEATURE:
<223> OTHER INFORMATION: cytoplasmic domain of ALK (human) with an
      inactivating mutation in the catalytic domain

<400> SEQUENCE: 3
gtgtaccgcc ggaagcacca ggagctgcaa gccatgcaga tggagctgca gagccctgag     60
tacaagctga gcaagctccg cacctcgacc atcatgaccg actacaaccc caactactgc    120
tttgctggca agacctcctc catcagtgac ctgaaggagg tgccgcggaa aaacatcacc    180
ctcattcggg gtctgggcca tggcgccttt gggggaggtgt atgaaggcca ggtgtccgga    240
atgcccaacg acccaagccc cctgcaagtg ctgtgagga cgctgcctga agtgtgctct    300
gaacaggacg aactggattt cctcatggaa gccctgatca tcagcaaatt caaccaccag    360
aacattgttc gctgcattgg ggtgagcctg caatccctgc cccggttcat cctgctggag    420
ctcatggcgg ggggagacct caagtccttc tccgagaga cccgccctcg cccgagccag    480
ccctcctccc tggccatgct ggaccttctg cacgtggctc gggacattgc ctgtggctgt    540
cagtatttgg aggaaaacca cttcatccac cgagacattg ctgccagaaa ctgcctcttg    600
acctgtccag gccctggaag agtggccaag attggagact cgggatggc ccgagacatc     660 tacagggcga gctactatag aaagggaggc tgtgccatgc tgccagttaa gtggatgccc    720
ccagaggcct tcatggaagg aatattcact tctaaaacag acacatggtc ctttggagtg    780
ctgctatggg aaatcttttc tcttggatat atgccatacc ccagcaaaag caaccaggaa    840
gttctggagt ttgtcaccag tggaggccgg atggacccac ccaagaactg ccctgggcct    900
gtataccgga taatgactca gtgctggcaa catcagcctg aagacaggcc caactttgcc    960
atcattttgg agaggattga atactgcacc caggacccgg atgtaatcaa caccgctttg   1020
ccgatagaat atggtccact tgtggaagag aagagaaag tgcctgtgag gcccaaggac    1080
cctgaggggg ttcctcctct cctggtctct caacaggcaa acggaggaggagcgcagc      1140 ccagctgccc caccacctct gcctaccacc tcctctggca aggctgcaaa gaaacccaca    1200
gctgcagaga tctctgttcg agtccctaga gggccggccg tggaagggggacacgtgaat    1260 atggcattct ctcagtccaa ccctcctcg gagttgcaca aggtccacgg atccagaaac    1320
aagcccacca gcttgtggaa cccaacgtac ggctcctggt ttacagagaa acccaccaaa    1380
```

```
aagaataatc ctatagcaaa gaaggagcca cacgacaggg gtaacctggg gctggaggga    1440
agctgtactg tcccacctaa cgttgcaact gggagacttc cggggggcctc actgctccta   1500 gagccctctt cgctgactgc caatatgaag gaggtacctc tgttcaggct acgtcacttc    1560
ccttgtggga atgtcaatta cggctaccag caacagggct tgcccttaga agccgctact    1620 gccctggag  ctggtcatta cgaggatacc attctgaaaa gcaagaatag catgaaccag    1680
cctgggccct ga                                                       1692

<210> SEQ ID NO 4
<211> LENGTH: 781
<212> TYPE: DNA
<213> ORGANISM: Artificial Sequence
<220> FEATURE:
<223> OTHER INFORMATION: GM-CSF sequence - human

<400> SEQUENCE: 4
acacagagag aaaggctaaa gttctctgga ggatgtggct gcagagcctg ctgctcttgg      60
gcactgtggc ctgcagcatc tctgcacccg cccgctcgcc cagccccagc acgcagccct    120
gggagcatgt gaatgccatc caggaggccc ggcgtctcct gaacctgagt agagacactg    180
ctgctgagat gaatgaaaca gtagaagtca tctcagaaat gtttgacctc caggagccga    240
cctgcctaca gacccgcctg agctgtaca  agcagggcct gcggggcagc ctcaccaagc    300
tcaagggccc cttgaccatg atggccagcc actacaagca gcactgccct ccaaccccgg    360
aaacttcctg tgcaacccag attatcacct ttgaaagttt caagagaaac ctgaaggact    420
ttctgcttgt catccccttt gactgctggg agccagtcca ggagtgagac cggccagatg    480
aggctggcca gccgggggag ctgctctctc atgaaacaag agctagaaac tcaggatggt    540
catcttggag ggaccaaggg gtgggccaca gccatggtgg gagtggcctg gacctgccct    600
gggccacact gaccctgata caggcatggc agaagaatgg gaatatttta tactgacaga    660
aatcagtaat atttatatat ttatattttt aaaatattta tttatttatt tatttaagtt    720
catattccat atttattcaa gatgttttac cgtaataatt attattaaaa atatgcttct    780
a                                                                   781

<210> SEQ ID NO 5
<211> LENGTH: 563
<212> TYPE: PRT
<213> ORGANISM: Artificial Sequence
<220> FEATURE:
<223> OTHER INFORMATION: entire cytoplasmic domain of the ALK protein -
      human

<400> SEQUENCE: 5

Val Tyr Arg Arg Lys His Gln Glu Leu Gln Ala Met Gln Met Glu Leu
 1               5                  10                  15

Gln Ser Pro Glu Tyr Lys Leu Ser Lys Leu Arg Thr Ser Thr Ile Met
            20                  25                  30

Thr Asp Tyr Asn Pro Asn Tyr Cys Phe Ala Gly Lys Thr Ser Ser Ile
        35                  40                  45

Ser Asp Leu Lys Glu Val Pro Arg Lys Asn Ile Thr Leu Ile Arg Gly
    50                  55                  60

Leu Gly His Gly Ala Phe Gly Glu Val Tyr Glu Gly Gln Val Ser Gly
65                  70                  75                  80

Met Pro Asn Asp Pro Ser Pro Leu Gln Val Ala Val Lys Thr Leu Pro
                85                  90                  95
```

-continued

Glu Val Cys Ser Glu Gln Asp Glu Leu Asp Phe Leu Met Glu Ala Leu
             100                 105                 110

Ile Ile Ser Lys Phe Asn His Gln Asn Ile Val Arg Cys Ile Gly Val
             115                 120                 125

Ser Leu Gln Ser Leu Pro Arg Phe Ile Leu Leu Glu Leu Met Ala Gly
             130                 135                 140

Gly Asp Leu Lys Ser Phe Leu Arg Glu Thr Arg Pro Arg Pro Ser Gln
145                 150                 155                 160

Pro Ser Ser Leu Ala Met Leu Asp Leu Leu His Val Ala Arg Asp Ile
                 165                 170                 175

Ala Cys Gly Cys Gln Tyr Leu Glu Glu Asn His Phe Ile His Arg Asp
             180                 185                 190

Ile Ala Ala Arg Asn Cys Leu Leu Thr Cys Pro Gly Pro Gly Arg Val
             195                 200                 205

Ala Lys Ile Gly Asp Phe Gly Met Ala Arg Asp Ile Tyr Arg Ala Ser
             210                 215                 220

Tyr Tyr Arg Lys Gly Gly Cys Ala Met Leu Pro Val Lys Trp Met Pro
225                 230                 235                 240

Pro Glu Ala Phe Met Glu Gly Ile Phe Thr Ser Lys Thr Asp Thr Trp
                 245                 250                 255

Ser Phe Gly Val Leu Leu Trp Glu Ile Phe Ser Leu Gly Tyr Met Pro
             260                 265                 270

Tyr Pro Ser Lys Ser Asn Gln Glu Val Leu Glu Phe Val Thr Ser Gly
             275                 280                 285

Gly Arg Met Asp Pro Pro Lys Asn Cys Pro Gly Pro Val Tyr Arg Ile
             290                 295                 300

Met Thr Gln Cys Trp Gln His Gln Pro Glu Asp Arg Pro Asn Phe Ala
305                 310                 315                 320

Ile Ile Leu Glu Arg Ile Glu Tyr Cys Thr Gln Asp Pro Asp Val Ile
                 325                 330                 335

Asn Thr Ala Leu Pro Ile Glu Tyr Gly Pro Leu Val Glu Glu Glu Glu
             340                 345                 350

Lys Val Pro Val Arg Pro Lys Asp Pro Glu Gly Val Pro Pro Leu Leu
             355                 360                 365

Val Ser Gln Gln Ala Lys Arg Glu Glu Glu Arg Ser Pro Ala Ala Pro
             370                 375                 380

Pro Pro Leu Pro Thr Thr Ser Ser Gly Lys Ala Ala Lys Lys Pro Thr
385                 390                 395                 400

Ala Ala Glu Val Ser Val Arg Val Pro Arg Gly Pro Ala Val Glu Gly
                 405                 410                 415

Gly His Val Asn Met Ala Phe Ser Gln Ser Asn Pro Pro Ser Glu Leu
             420                 425                 430

His Lys Val His Gly Ser Arg Asn Lys Pro Thr Ser Leu Trp Asn Pro
             435                 440                 445

Thr Tyr Gly Ser Trp Phe Thr Glu Lys Pro Thr Lys Lys Asn Asn Pro
             450                 455                 460

Ile Ala Lys Lys Glu Pro His Asp Arg Gly Asn Leu Gly Leu Glu Gly
465                 470                 475                 480

Ser Cys Thr Val Pro Pro Asn Val Ala Thr Gly Arg Leu Pro Gly Ala
                 485                 490                 495

Ser Leu Leu Leu Glu Pro Ser Ser Leu Thr Ala Asn Met Lys Glu Val
             500                 505                 510

Pro Leu Phe Arg Leu Arg His Phe Pro Cys Gly Asn Val Asn Tyr Gly
               515                 520                 525

Tyr Gln Gln Gln Gly Leu Pro Leu Glu Ala Ala Thr Ala Pro Gly Ala
       530                 535                 540

Gly His Tyr Glu Asp Thr Ile Leu Lys Ser Lys Asn Ser Met Asn Gln
545                 550                 555                 560

Pro Gly Pro

<210> SEQ ID NO 6
<211> LENGTH: 144
<212> TYPE: PRT
<213> ORGANISM: Artificial Sequence
<220> FEATURE:
<223> OTHER INFORMATION: recombinant GM-CSF - human

<400> SEQUENCE: 6

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
        130                 135                 140

<210> SEQ ID NO 7
<211> LENGTH: 1692
<212> TYPE: DNA
<213> ORGANISM: Artificial Sequence
<220> FEATURE:
<223> OTHER INFORMATION: entire intracytoplasmatic domain of ALK
      protein - human

<400> SEQUENCE: 7
gtgtaccgcc ggaagcacca ggagctgcaa gccatgcaga tggagctgca gagccctgag       60
tacaagctga gcaagctccg cacctcgacc atcatgaccg actacaaccc caactactgc      120
tttgctggca agacctcctc catcagtgac ctgaaggagg tgccgcggaa aaacatcacc      180
ctcattcggg gtctgggcca tggcgccttt gggaaggtgt atgaaggcca ggtgtccgga      240
atgcccaacg acccaagccc cctgcaagtg gctgtgaaga cgctgcctga agtgtgctct      300
gaacaggacg aactggattt cctcatggaa gccctgatca tcagcaaatt caaccaccag      360
aacattgttc gctgcattgg ggtgagcctg caatccctgc cccggttcat cctgctggag      420
ctcatggcgg ggggagacct caagtccttc ctccgagaga cccgcccctcg cccgagccag      480 ccctcctccc tggccatgct ggaccttctg cacgtggctc gggacattgc ctgtggctgt      540
cagtatttgg aggaaaacca cttcatccac cgagacattg ctgccagaaa ctgcctcttg      600

```
acctgtccag gccctggaag agtggccaag attggagact tcgggatggc ccgagacatc    660
tacagggcga gctactatag aaagggaggc tgtgccatgc tgccagttaa gtggatgccc    720
ccagaggcct tcatggaagg aatattcact tctaaaacag acacatggtc ctttggagtg    780
ctgctatggg aaatcttttc tcttggatat atgccatacc ccagcaaaag caaccaggaa    840
gttctggagt ttgtcaccag tggaggccgg atggacccac ccaagaactg ccctgggcct    900
gtataccgga taatgactca gtgctggcaa catcagcctg aagacaggcc caactttgcc    960
atcattttgg agaggattga atactgcacc caggacccgg atgtaatcaa caccgctttg   1020
ccgatagaat atggtccact tgtggaagag gaagagaaag tgcctgtgag gcccaaggac   1080 cctgagggg ttcctcctct cctggtctct caacaggcaa aacgggagga ggagcgcagc    1140
ccagctgccc caccacctct gcctaccacc tcctctggca aggctgcaaa gaaacccaca   1200
gctgcagaga tctctgttcg agtccctaga gggccggccg tggaaggggg acacgtgaat   1260
atggcattct ctcagtccaa ccctccttcg gagttgcaca aggtccacgg atccagaaac   1320
aagcccacca gcttgtggaa cccaacgtac ggctcctggt ttacagagaa acccaccaaa   1380
aagaataatc ctatagcaaa gaaggagcca cacgacaggg gtaacctggg gctggaggga   1440
agctgtactg tcccacctaa cgttgcaact gggagacttc cgggggcctc actgctccta   1500
gagccctctt cgctgactgc caatatgaag gaggtacctc tgttcaggct acgtcacttc   1560
ccttgtggga atgtcaatta cggctaccag caacagggct tgcccttaga agccgctact   1620
gcccctggag ctggtcatta cgaggatacc attctgaaaa gcaagaatag catgaaccag   1680
cctgggccct ga                                                       1692
```

ANAPLASTIC LYMPHOMA KINASE (ALK) AS ONCOANTIGEN FOR LYMPHOMA VACCINATION

CROSS REFERENCE TO RELATED APPLICATION

This application claims the benefit of U.S. Provisional Application No. 60/960,414 filed on Sep. 28, 2007, incorporated herein by reference in its entirety.

FIELD OF THE INVENTION

The present disclosure concerns tumor vaccines for the treatment and/or prevention of tumors in a human subject.

BACKGROUND OF THE INVENTION

An ideal vaccination strategy against tumors relies on immunogenic specific antigens that are absolutely required for tumor maintenance. So far vaccination with patient-specific immunoglobulin idiotypes has given the most promising results in cancer vaccination.

Vaccines in cancer prevention and in combinational protocols in oncology have provided great promises, although often followed by recurring pessimism. The reasons for this lack of effectiveness rely mainly in the difficult identification of specific tumor antigens essential for tumor growth.

SUMMARY OF THE INVENTION

The need is therefore felt for the identification of an oncoantigen that can be used in the preparation of efficacious tumor vaccine for the treatment and prevention of tumor in a human subject.

The object of the present disclosure is providing such an oncoantigen.

According to the invention, the above object is achieved thanks to the subject matter recalled specifically in the ensuing claims, which are understood as forming an integral part of this disclosure.

An embodiment of the present disclosure provides the use of intracytoplasmatic domain of Anaplastic Lymphoma Kinase (ALK) protein and/or a nucleic acid molecule encoding for the intracytoplasmatic domain of Anaplastic Lymphoma Kinase (ALK) protein, of any species, for the preparation of a medicament, preferably a vaccine, for the treatment and/or prevention of a tumor in a subject, preferably a lymphoma or a carcinoma.

A further embodiment of the present disclosure provides the use of nucleic acid molecule(s) encoding for the intracytoplasmatic domain of Anaplastic Lymphoma Kinase (ALK) protein of any species in combination with a nucleic acid molecule encoding for Granulocyte-Monocytes Colony Stimulating Factor (GM-CSF) for the preparation of a medicament, preferably a vaccine, for the treatment and/or prevention of a tumor in a subject.

A still further embodiment of the present disclosure provides a product containing nucleic acid molecule(s) encoding for the intracytoplasmatic domain of Anaplastic Lymphoma Kinase (ALK) protein of any species and at least one chemotherapeutic agent or at least one (small molecule) kinase inhibitor as a combined preparation for simultaneous, separate or sequential use in the treatment and/or prevention of a tumor in a subject.

BRIEF DESCRIPTION OF THE DRAWINGS

The invention will now be described, by way of example only, with reference to the enclosed figures of drawing, wherein.

DETAILED DESCRIPTION OF EXEMPLARY EMBODIMENTS

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

The present disclosure demonstrates that the DNA vaccination with plasmids encoding for the cytoplasmic domain of Anaplastic Lymphoma Kinase (ALK), which is translocated in different fusion proteins necessary for the maintenance of Anaplastic Large Cell Lymphoma (ALCL) growth, protects mice from local and systemic lymphoma growth.

The tumor protection after ALK vaccination was potent and long lasting, eliciting an ALK specific, IFNγ and CD8 T-cell mediated cytotoxicity.

Furthermore, a combination of chemotherapy and vaccination significantly enhanced the survival of mice by eradicating NPM-ALK lymphomas.

These findings indicate that ALK represents an ideal tumor antigen for vaccination-based therapies of ALCLs and possibly of other ALK expressing human tumors.

Figure 1A:
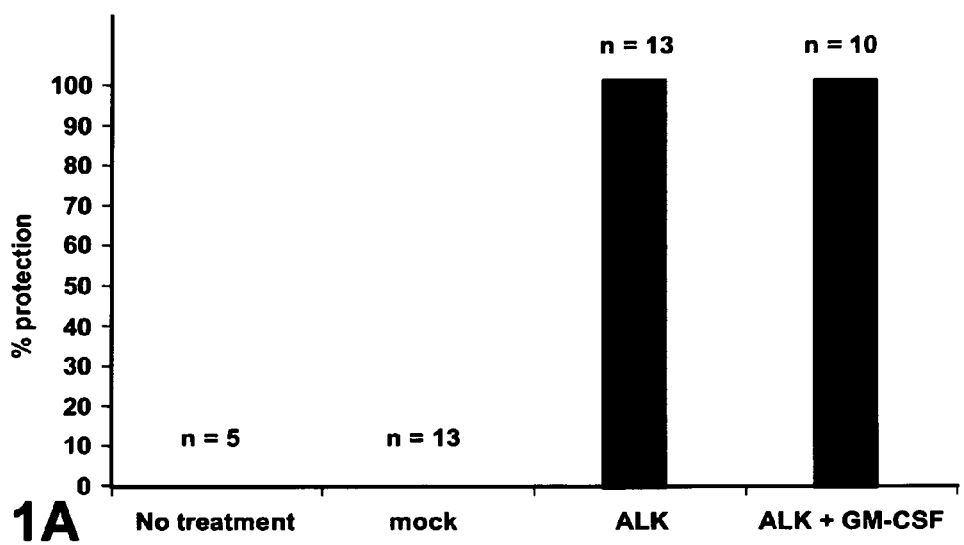
FIG. 1. ALK vaccination prevents the growth of NPM-ALK positive lymphoma cells. (a,b) BALB/c mice were vaccinated on day 0 and 7 in both the tibial muscles with 40 µg of pDEST plasmid or with pDEST-ALK (ALK) plasmid coding for the full ALK tyrosine kinase intracytoplasmic domain (a) or with pDEST-ALKt (ALKt) coding for a truncated portion of ALK lacking the part of the tyrosine kinase domain (b). An additional group of mice was vaccinated with the pDEST-ALK or pDEST-ALKt plasmids combined with the same amount of a pcDNA3 plasmid coding for GM-CSF. On day 14, mice were challenged with $1 \times 10^6$ NP-ALK expressing lymphoma cells derived from NPM-ALK BALB/c Tg mice injected subcutaneously (s.c) in the right flank. (c) BALB/c mice were DNA vaccinated as above with a pDEST-ALK plasmid. After 7 months from vaccination mice were tumor challenged as above. The histograms represent the percentages of mice which were protected from tumor uptake 60 days after the challenge. The total numbers of mice from two to four independent experiments are indicated. (d) Sequential histology of NPM-ALK lymphoma cell growth in mock and ALK-vaccinated BALB/c mice injected in the flank (hematoxylin and eosin stains). Arrows indicate the reactive inguinal lymph node, * indicate tumors (e) Histological examinations (top panels, hematoxylin and eosin stainings) and anti-ALK immunohistochemistry (bottom panels) of subcutaneous lymphomas at day 10 after injection in mock or ALK vaccinated mice. Infiltration of reactive cells, mainly lymphocytes and granulocytes, are evident only in ALK vaccinated mice. Scale bars, 30 µm.
Figure 1B:
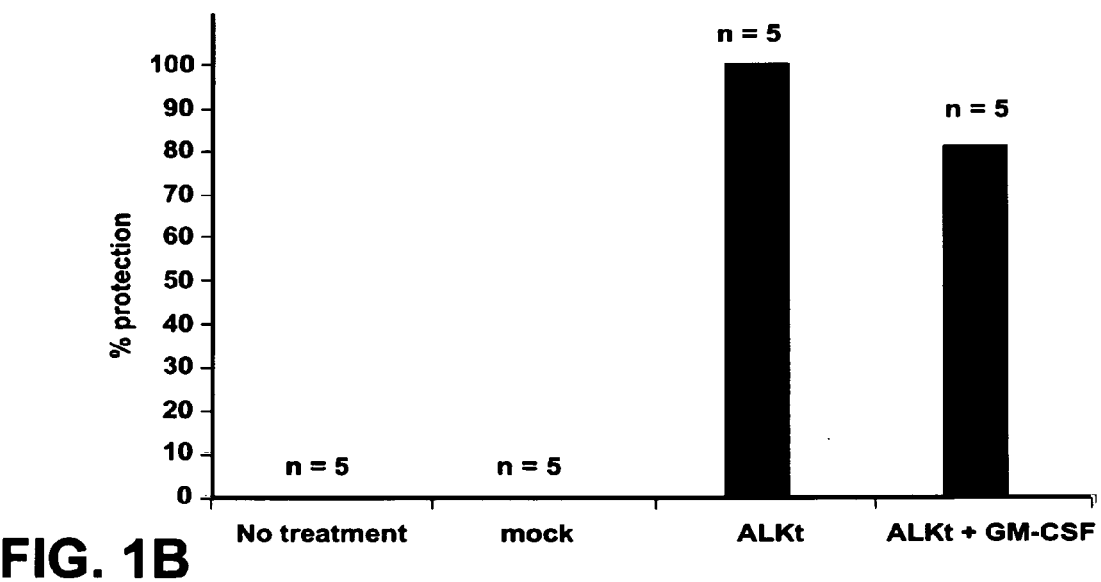

BALB/c mice were vaccinated twice within a week interval with a DNA plasmid coding for the intracytoplasmic domain of ALK alone, or mixed with a second plasmid encoding for the Granulocyte-Monocytes Colony Stimulating Factor (GM-CSF), Alternatively, animals were immunized with plasmids encoding for a truncated portion of the intracytoplasmic domain of ALK (ALKt), lacking part of its catalytic domain, or for the ALK$^{K210R}$ dead mutant, which lacks its tyrosine kinase activity. One week after the second vaccination, the animals were challenged subcutaneously with a lethal dose of syngeneic NPM-ALK expressing lymphoma cells. Two different lymphoma cell lines, established from BALB/c NPM-ALK transgenic (Tg) mice were utilized. A localized lymphoma mass grew by 10-15 days after Injection in all control mice and in animals vaccinated with the empty plasmid, while a total protection was observed in mice vaccinated with the complete ALK or with the ALKt plasmid or with the dead mutant ALK$^{K210R}$ construct (FIGS. 1a,b and 5).

Thus, DNA vaccination with the intracytoplasmatic domain of ALK plasmid is efficient also when the plasmid codes for a protein with reduced (<20% of the wild type protein) or absent catalytic function.

A similar protection is achieved after vaccination with DNA sequences derived from species with high homology (equal or greater than 80%) to the DNA sequence encoding for the entire intracytoplasmatic portion of human ALK (as shown in SEQ ID No.:7), such as Pan troglodytes, Macaca mulatta, Microcebus murinus, Felis catus, Canis familiaris, Tupaia belangeri, Bos Taurus, Rattus norvegicus, Mus musculus, Monodelphis domestica, or Gallus gallus.

Figure 1C:
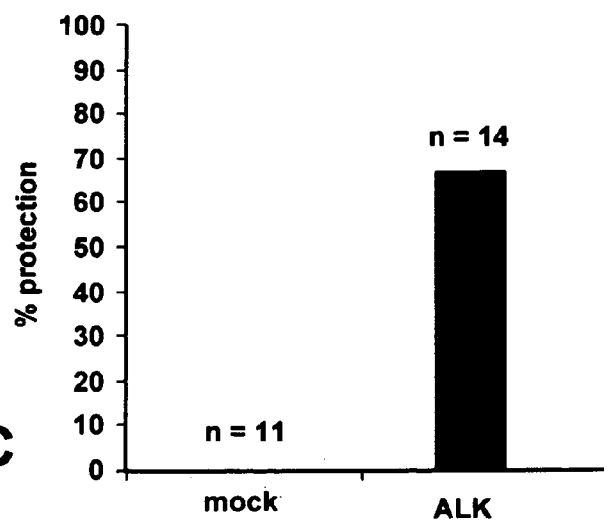
Figure 1D:
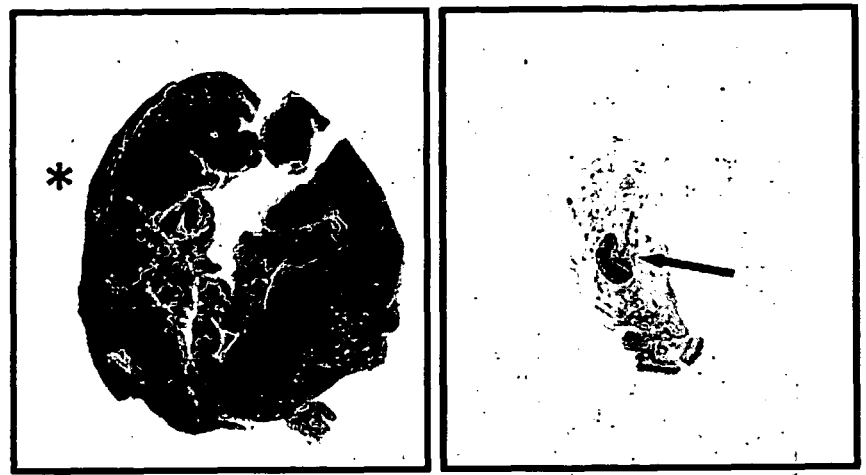
Figure 1D:
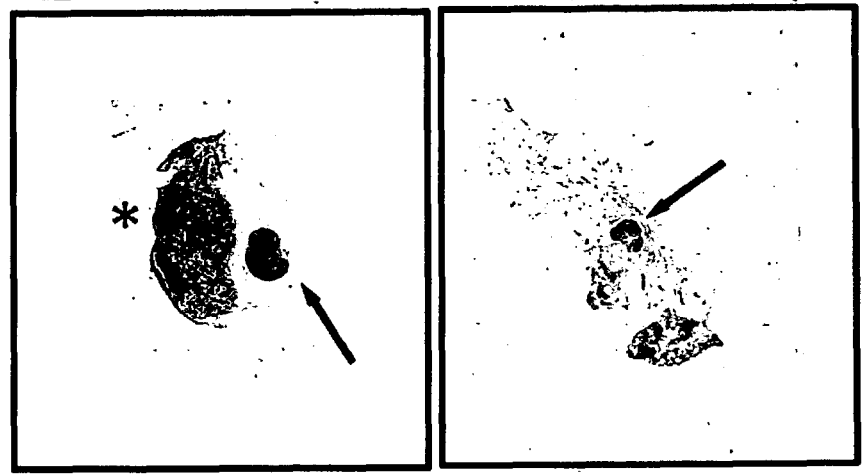
Figure 1D:
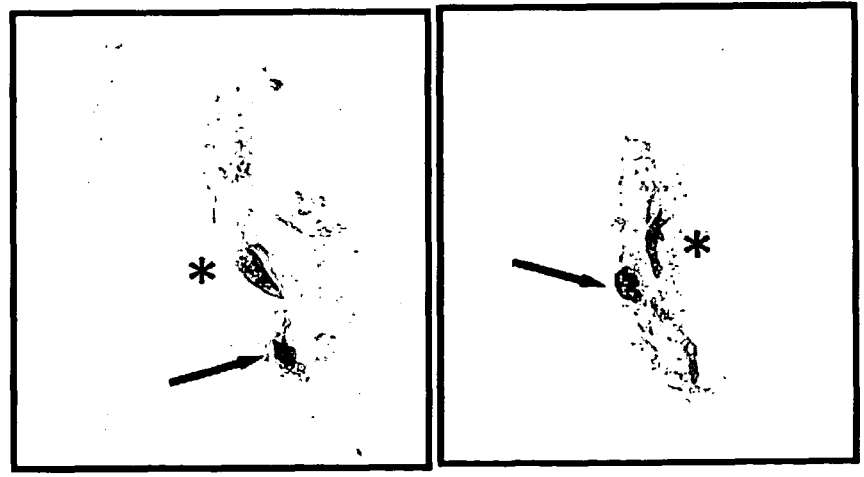
Figure 1E:
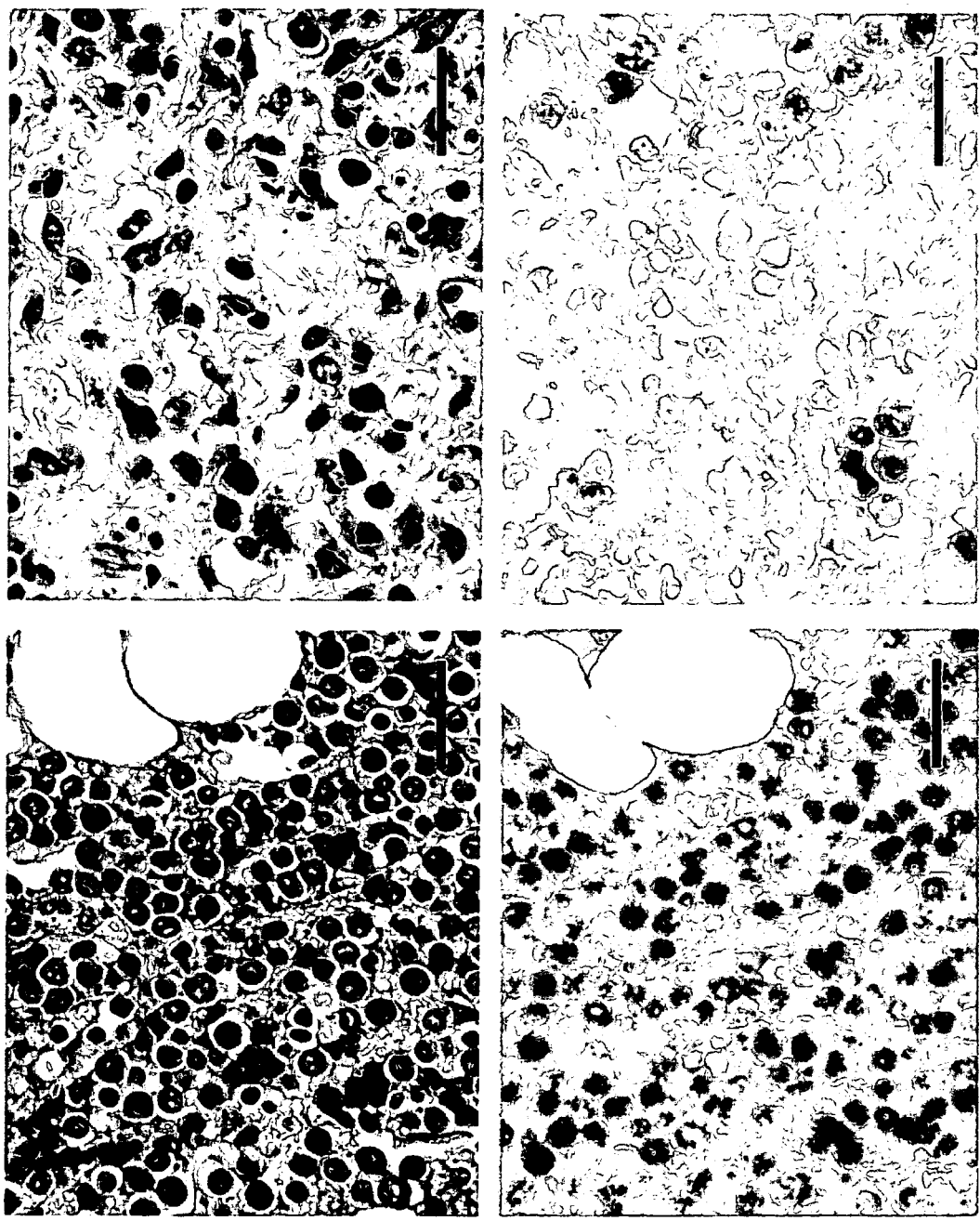

Identical protection rates were observed against the challenge with a second NPM-ALK expressing lymphoma cell line. Notably, two ALK vaccinations elicited a long lasting immune response, granting a significant tumor protection up to 7 months (FIG. 1c). Sequential histological biopsies showed that in mock vaccinated mice the lymphoma grew progressively overtime in the absence of any significant reactive infiltrate. By contrast, in ALK vaccinated mice, an inflammatory reaction mainly composed of lymphocytes and granulocytes was intermingled with NPM-ALK positive lymphoma cells within the first ten days after the tumor challenge (FIG. 1d) and by day 14 all neoplastic cells were successfully cleared (FIG. 1e).

Figure 2A:
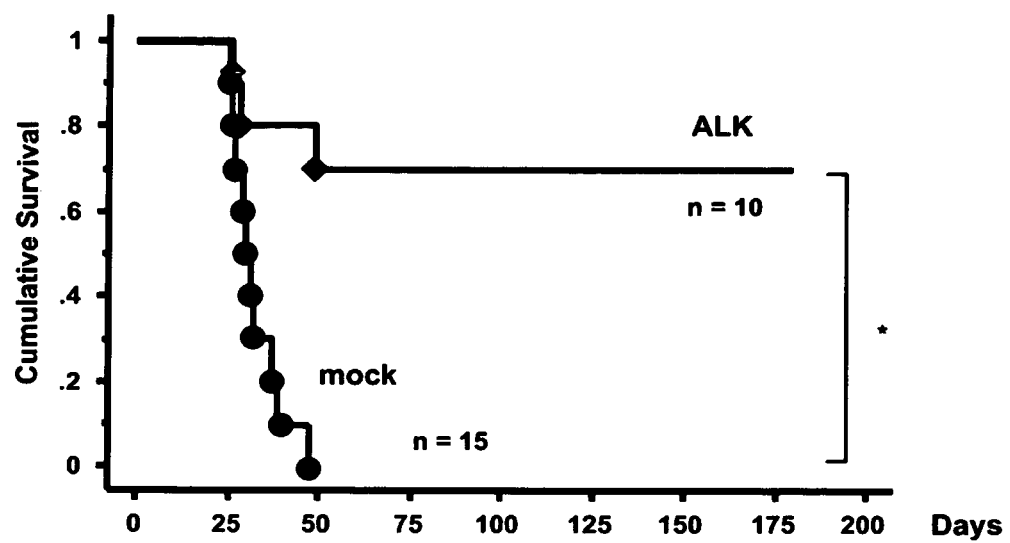
FIG. 2. Efficacy of ALK vaccination in preventing disseminated lymphoma growth and in lymphoma therapy (a,b) Disseminated growth of NPM-ALK lymphoma cells injected in the tail vein in mock or ALK plasmid vaccinated BALB/c mice. (a) All mock vaccinated mice challenged i.v. 7 days after the second vaccination with $1 \times 10^6$ NPM-ALK lymphoma died of lymphoma outgrowth within 50 days after challenge while 70% of ALK vaccinated mice remained alive and well for all the observation period of 180 days. Data are from one of two independent experiments with similar results. * P=0.0061 (b) Autopsies of mock vaccinated mice displayed lymphoma cells disseminated in the kidney, the spleen and the liver. By contrast, ALK plasmid vaccinated mice were tumor free in all the organs. (c) Increasing amounts of NPM-ALK lymphoma cells were injected s.c. in BALB/c mice on day 0. Mice were then vaccinated as described above on days 1 and 8. Tumor growth was followed over time. Data are from one of two independent experiments with at least 7 mice for each group. * P<0.01. (d) BALB/c mice were i.v. injected with $1 \times 10^6$ NPM-ALK lymphoma cells on day 0. On day 7 mice received i.v. 10 mg/kg of doxorubicin (dashed arrow) followed on days 14, 21 and 28 by DNA vaccination with empty (mock) or ALK-expressing plasmids (full arrows). Mice were then followed up to 90 days. Data are collected from two independent experiments showing similar results. * P<0.05. (e) Efficacy of ALK vaccination in chemotherapy treated mice. BALB/c mice were injected i.v. with 10 mg/kg doxorubicin on day 0 and vaccinated with the indicated plasmids on days 7, 14 and 21. $1 \times 10^6$ NPM-ALK expressing lymphoma cells were then injected s.c. 60 days after the last vaccination. Percentages of protected mice are indicated. Data are from one of two independent experiments. (f) Efficacy of ALK vaccination on lymphoma growth in mice treated with ALK selective inhibitor. BALB/c mice were s.c. injected with 1×10⁶ NPM-ALK lymphoma cells on day 0. When tumor reached approx 2 cm in maximum diameter, mice were treated with an oral ALK kinase inhibitor for 15 days (30 or 100 mg/kg bid). Tumor size was measured over time. (g) Efficacy of combination therapy based on ALK selective inhibitor and ALK vaccination. BALB/c mice were s.c. injected with 1×10⁶ NPM-ALK lymphoma cells on day 0. When tumor reached approx 2 cm in maximum diameter, mice were treated with an oral ALK kinase inhibitor for 15 days (30 or 100 mg/kg bid). When tumor size decrease to less than 0.5 cm mice were vaccinated as described above. Percentages of cure mice are indicated.
Figure 2B:
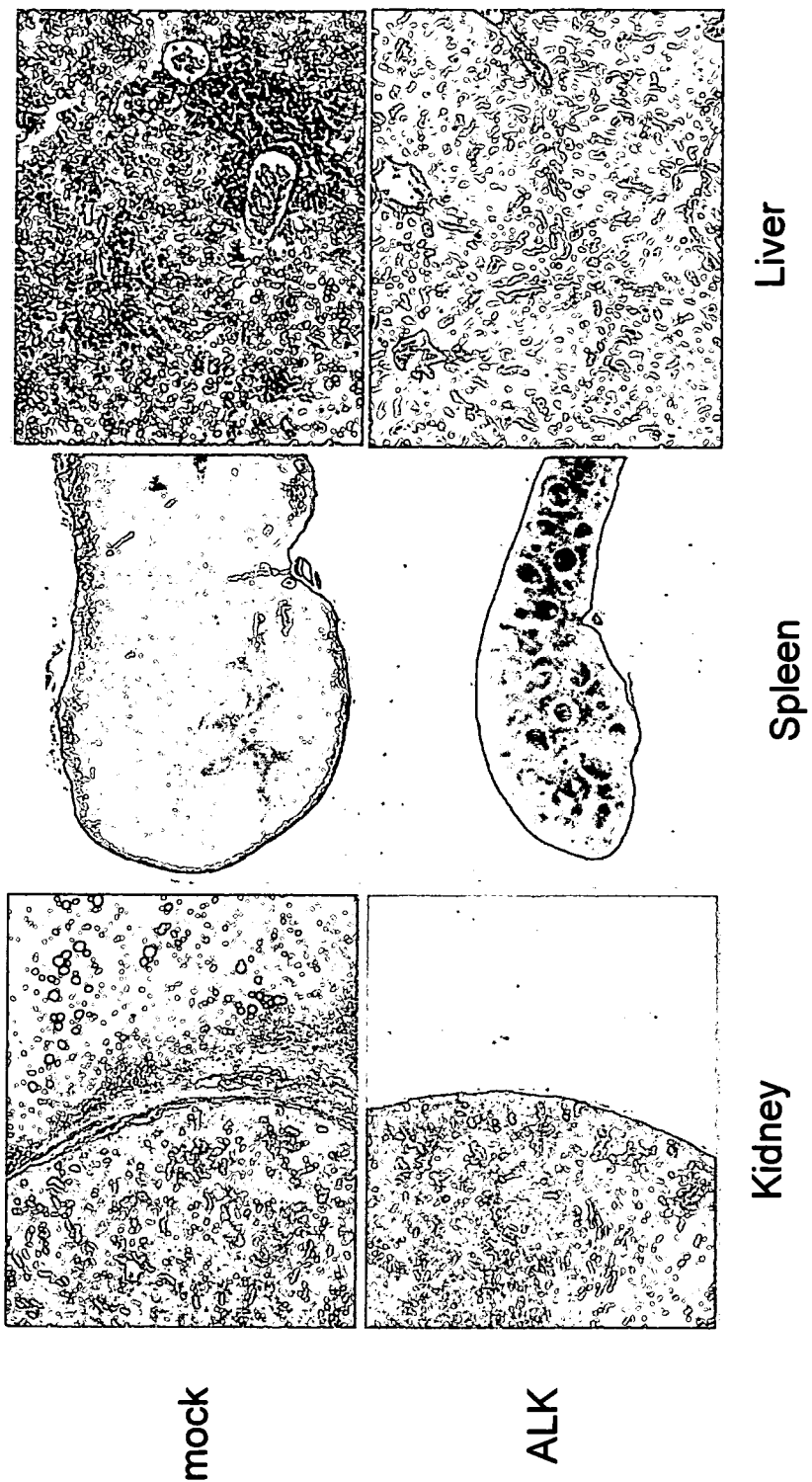

Since lymphomas are almost invariably systemic diseases, the efficacy of ALK DNA immunization in controlling the disseminated lymphoma growth was studied. Mice were immunized twice, as described above, and subsequently challenged with 1×10$^6$ NPM-ALK positive lymphoma cells by tail vein injection. All mock-vaccinated mice died by day 50 because of a massive and systemic disease, involving the central nervous system (the cerebellum and the meningeal spaces), soft tissues, and many other organs, including the heart, the spleen, the liver and the kidney; whereas 70% of the ALK vaccinated mice were protected and were healthy up to 180 days (FIGS. 2a,b).

Figure 2C:
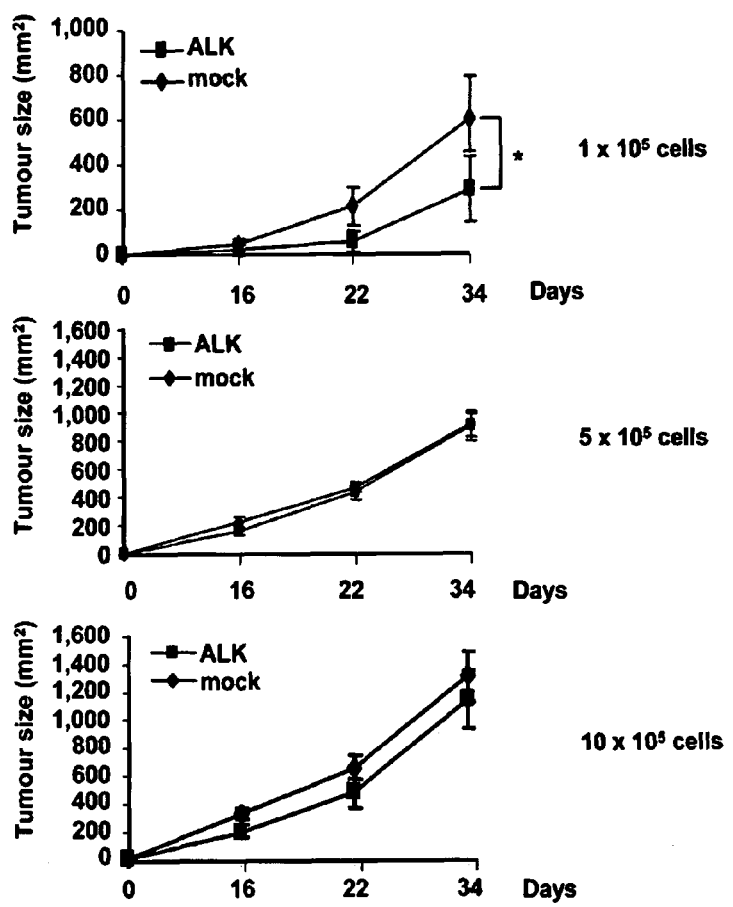

Next, it has been tested whether DNA-based ALK vaccines could be employed as a therapeutic strategy. Mice were first injected s.c. with lymphoma cells and then vaccinated twice at one week interval Whereas ALK vaccination did not control lymphoma growth when 1×10$^6$ or 5×10$^5$ lymphoma cells were injected, a significant protection was observed when 1×10$^5$ cells were inoculated, indicating a therapeutic potential of the vaccine only in animals with limited tumor burden (FIG. 2c). This limited tumor burden could be compared to non-Hodgkin's lymphomas (NHL) patients with minimal residual disease after chemotherapy.

Figure 6:
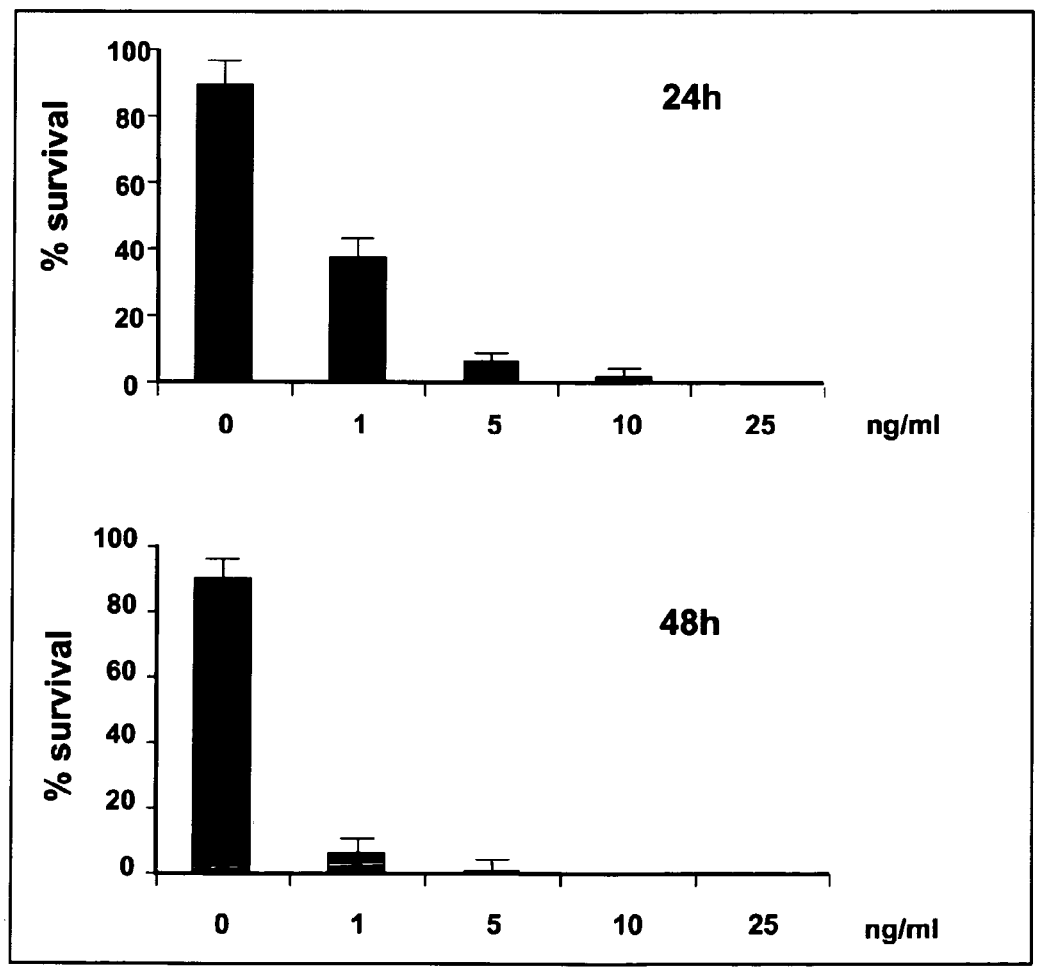
FIG. 6. NPM-ALK lymphoma cells are sensitive to doxorubicin. NPM-ALK lymphoma cells were incubated in vitro for 24 or 48 hours with increasing concentrations of doxorubicin. Percentages of alive cells were calculated by TMRM staining and flow cytometry analyses.
Figure 7:
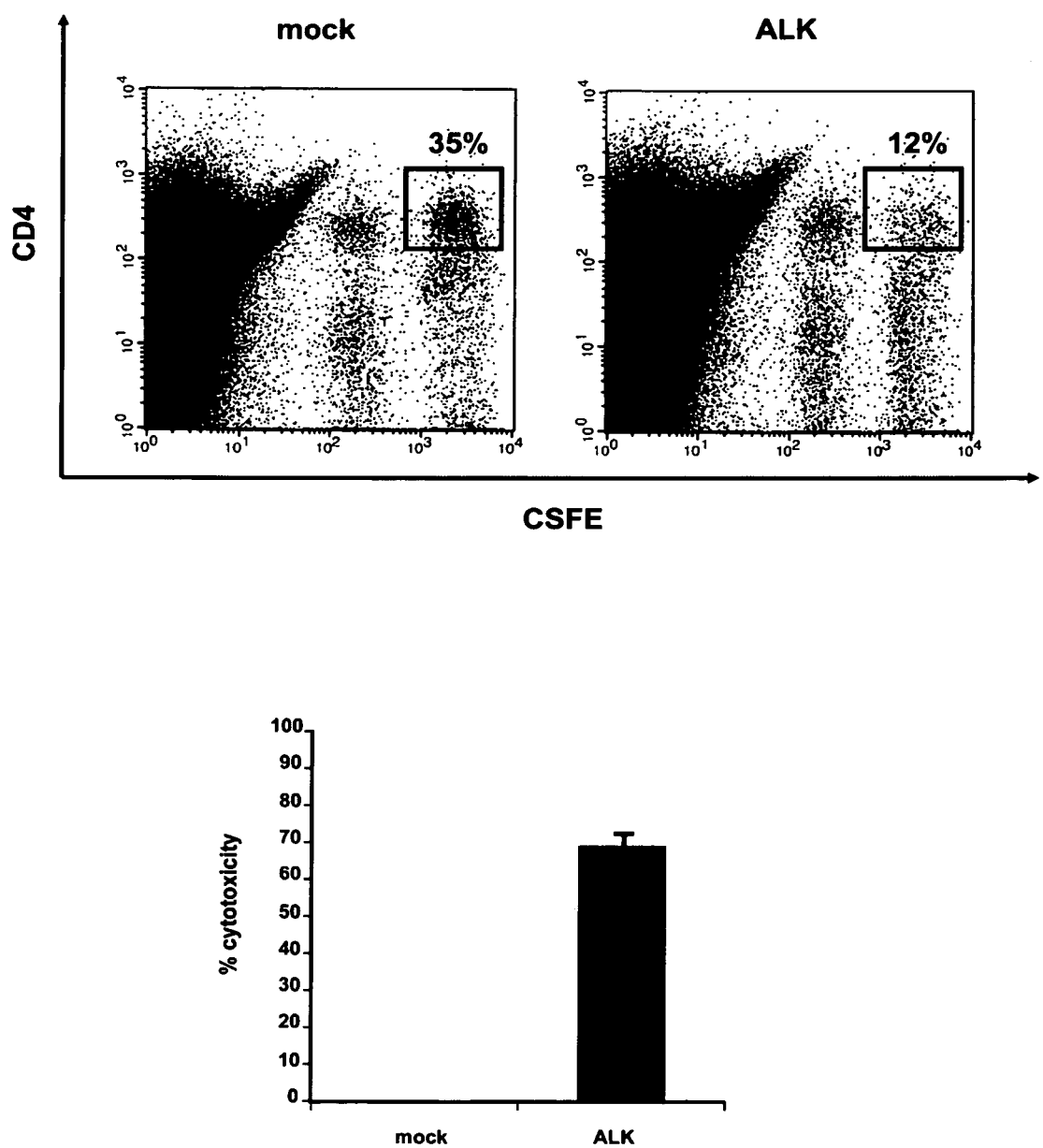
FIG. 7. Long lasting protection after DNA vaccination. BALB/c mice were vaccinated twice as indicated above with control or ALK-expressing plasmids. Six months after the last vaccination in vivo cytotoxic assay was performed as described in FIG. 3. Mice were sacrificed and percentages of CD4+CSFE+expressing splenocytes were analysed by flow cytometry (top panels). Percentages of ALK-directed specific cytotoxicity were calculated by normalizing the numbers of NPM-ALK expressing CD4 T-cells (CSFE high) with the total amount of CD4+CSFE+ T-cells (low panel).

To mimic more strictly these clinical settings, the efficiency of the vaccination strategy disclosed herein in association with chemotherapy, which remains the standard therapeutic strategy for human Anaplastic Large Cell Lymphomas (ALCL), was tested. Since current ALCL protocols are based on multiple chemotherapeutic agents such as prednisolone, cyclophosphamide, doxorubicin, methotrexate, and vincristine, some of these drugs were tested in vitro and demonstrated that murine NPM-ALK expressing lymphoma cells underwent rapid apoptosis with low doses of doxorubicin (FIG. 6).

Figure 2D:
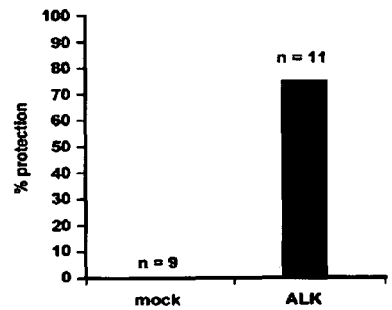

Given that chemotherapy can severely compromise the immune system, the present inventors subsequently demonstrated that doxorubicin-treated animals, following ALK DNA vaccination, were efficiently protected once challenged with lymphoma cells (FIG. 2d).

Figure 2E:
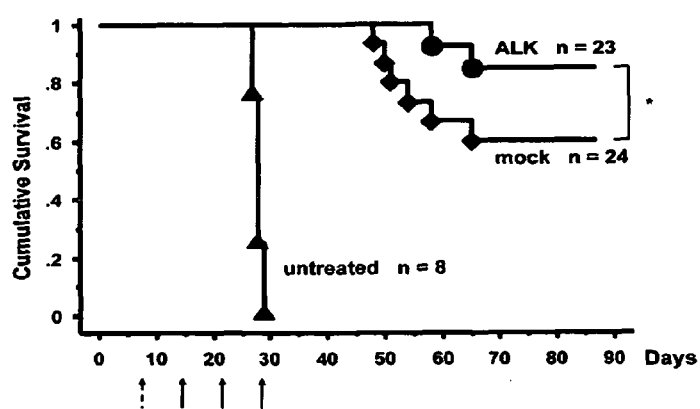

To test the efficiency of the DNA vaccination after a single-drug based regimen, the present inventors injected i.v. 1×10$^6$ lymphoma cells and after one week the mice were treated with a single dose of doxorubicin. After 7 more days, animals were vaccinated with either control or ALK vectors for three times at one week interval. Untreated mice died rapidly in less than 35 days, but chemotherapy alone prolonged their survival, with a cure rate of 60%, similarly to those currently achieved in ALCL patients. Remarkably, the combination of chemotherapy with the ALK vaccination significantly increased to 87% the fraction of cured mice (FIG. 2e).

High dose and/or multi-drug combination chemotherapy protocols are associated with significant toxicity and an increased risk of secondary neoplasms, particularly in young cancer patients. Since NPM-ALK lymphoma cells are highly sensitive to small drug ALK inhibitors, mice bearing syngeneic xenograft tumors were treated with an oral ALK kinase inhibitor for 15 days (30 or 100 mg/kg bid). In virtually all animals, this protocol led to a substantial reduction of the neoplastic masses (FIG. 2f) and to a high degree of intra-tumor necrosis.

Figure 2G:
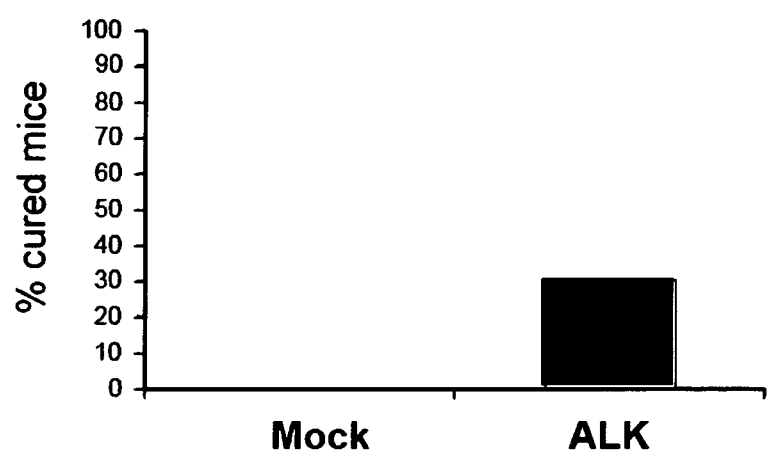

To test whether the DNA vaccination could synergize with the therapy with anti-ALK inhibitors and improve the overall survival of mice bearing NPM-ALK lymphomas, mice were vaccinated with ALK or mock plasmids after reduction of tumor mass with ALK inhibitors similarly to those depicted in FIG. 2f and followed their rate of relapse, tumor growth and overall survival. As shown in FIG. 2g, ALK DATA vaccination post ALK inhibitor treatment delays tumor growth in relapsing mice and leads to a 30% cure rate.

Figure 3A:
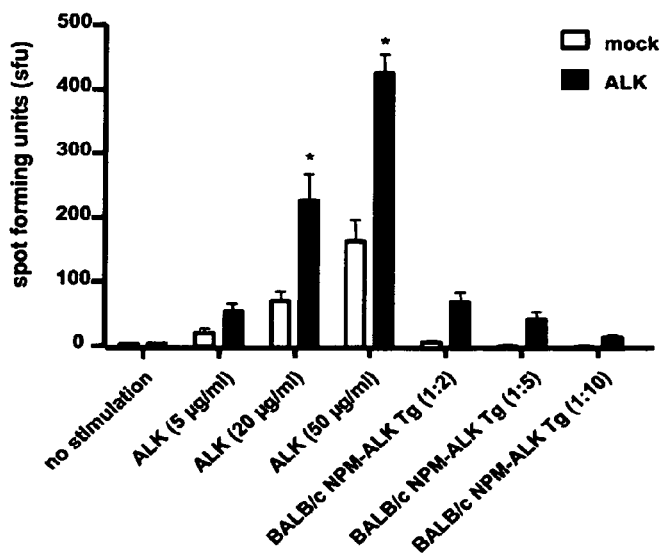
FIG. 3. Cytotoxic activity and IFNγ production in ALK-vaccinated mice. (a) Spleen cells from BALB/c mice vaccinated as above were cultured with the indicated amounts of recombinant murine ALK protein or with the indicated ratios of NPM-ALK Tg BALB/c splenocytes. Spot forming units for IFNγ production were evaluated by Elispot. * $P<0.01$ (b,c) In vivo cytotoxicity assay. BALB/c mice vaccinated twice with the indicated plasmids were i.v. injected with 10⁷ wild type mixed with 10⁷ NPM-ALK Tg BALB/c splenocytes labeled with different amounts of CFSE (0.5 μM and 5 μm, respectively). (b) After 72 hours mice were sacrificed and percentages of CD4+CSFE+ expressing splenocytes were analyzed by flow cytometry. (c) Percentages of ALK-directed specific cytotoxicity were calculated by normalizing the numbers of NPM-ALK expressing CD4 T-cells (CSFE high) with the total amount of CD4+CSFE+ T-cells. (d) Visualization of in vivo ALK-directed cytotoxicity. Spleens from vaccinated mice injected with NPM-ALK Tg BALB/c splenocytes as above were immunostained with anti-ALK antibody to detected the transferred cells. Significantly less ALK positive cells were detected in ALK vaccinated mice as compared to controls. Boxed areas in the top panels are magnified in the lower panels. Scale bars, 200 μM FIG. 4. Protection generated by ALK vaccination requires CD8 T cells and IFNγ production, but not B cells. (a) BALB/c, BALB-Igμ-chain, BALB-IFNγ −/− and BALB-perforin −/− mice were vaccinated with the mock or ALK plasmid twice on days 0 and 7 and then challenged on day 14 with 1×10⁶ NPM-ALK lymphoma cells s.c. Tumor growth was followed over time. Bars represent standard errors. (b) In vivo cytotoxicity assays were performed as described in FIG. 3 with BALB/c, BALB-Igμ-chain, BALB-IFNγ −/− and BALB-perforin −/− mice vaccinated with the pDEST-ALK plasmid. (c) BALB/c mice were vaccinated twice on days 0 and 7, as described above, and depleted of either CD8 or CD4 T cells with two consecutive injections on days 14 and 15. NPM-ALK lymphoma cells (1×10⁶) were then injected s.c. on day 29 and tumor growth was followed at the indicated times. * $P<0.001$ for CD4 versus CD8 depleted ALK vaccinated mice. Bars represent standard errors.
Figure 3B:
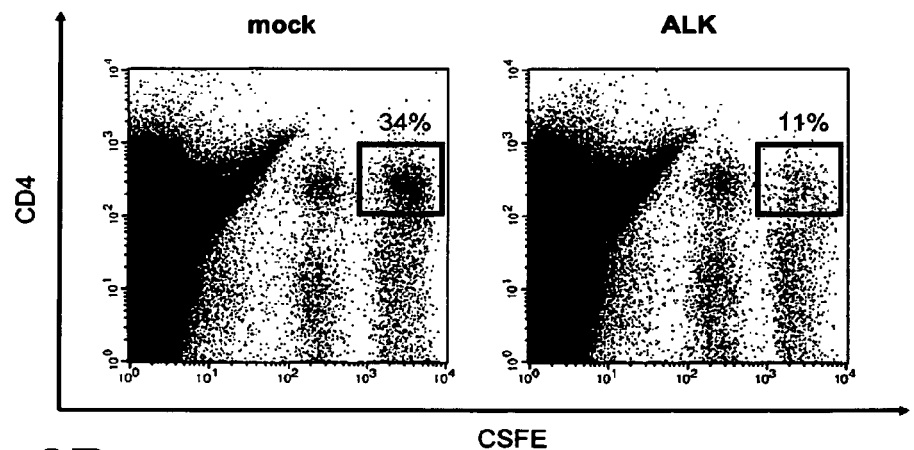
Figure 3C:
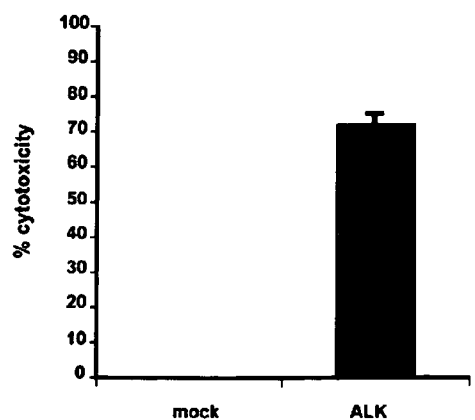
Figure 3D:
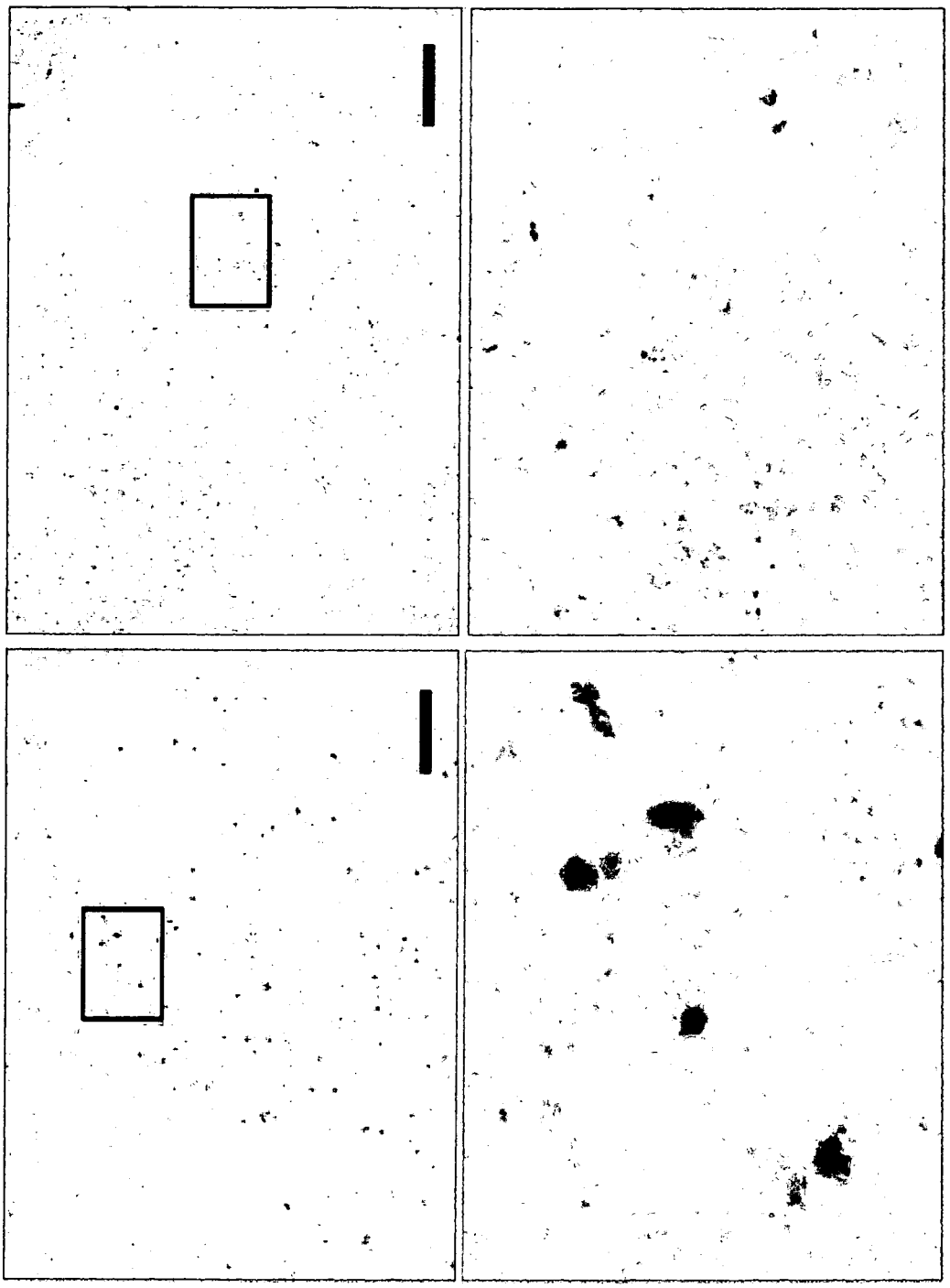
Figure 5:
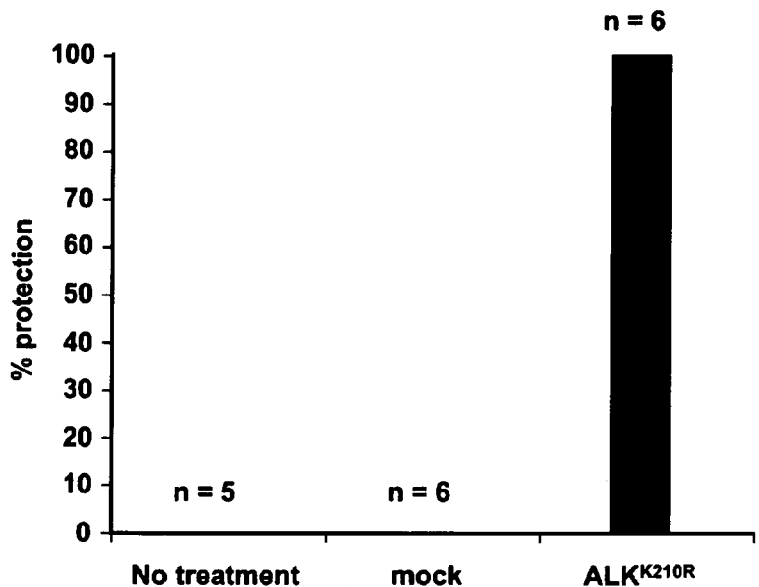
FIG. 5. DNA-based vaccination with ALK$^{K210R}$ plasmid protects from lymphoma growth. BALB/c mice were DNA vaccinated twice on days 0 and 7 with 40 μg of pDEST empty vector (mock) or pDEST-ALK$^{K210R}$ (ALK$^{K210R}$) plasmids in which the entire cytoplasmic portion of a kinase dead mutant K210R of the ALK tyrosine kinase was cloned. On day 14, 1×10⁶ NPM-ALK lymphoma cells were injected s.c. Protection is indicated as the percentage of mice which did not show tumor uptake after 60 days. One of two independent experiments is represented.

The mechanisms of tumor protection by vaccines are multiple. Since the majority of the antitumoral immune reactions are associated with IFNγ production, the present inventors first demonstrated that the percentages of splenic lymphocytes releasing IFNγ from ALK vaccinate animals was remarkably expanded as compared to controls after stimulation by an ALK recombinant protein or NPM-ALK expressing BALB/c lymphocytes in vitro (FIG. 3a). Next, DNA vaccinated mice were tested for their ability to generate a specific cytotoxic response against ALK positive cells in vivo. BALB/c wild type and NPM-ALK Tg splenocytes labeled with different doses of CSFE were injected in vaccinated mice. After 3 days, ALK-vaccinated mice exhibited a marked and specific cytotoxic activity only against NPM-ALK but not wild type splenocytes as NPM-ALK expressing splenocytes were selectively decreased in ALK vaccinated mice compared to controls, as detected by flow cytometry or immunohistochemistry (FIG. 3b-d).

Figure 8A:
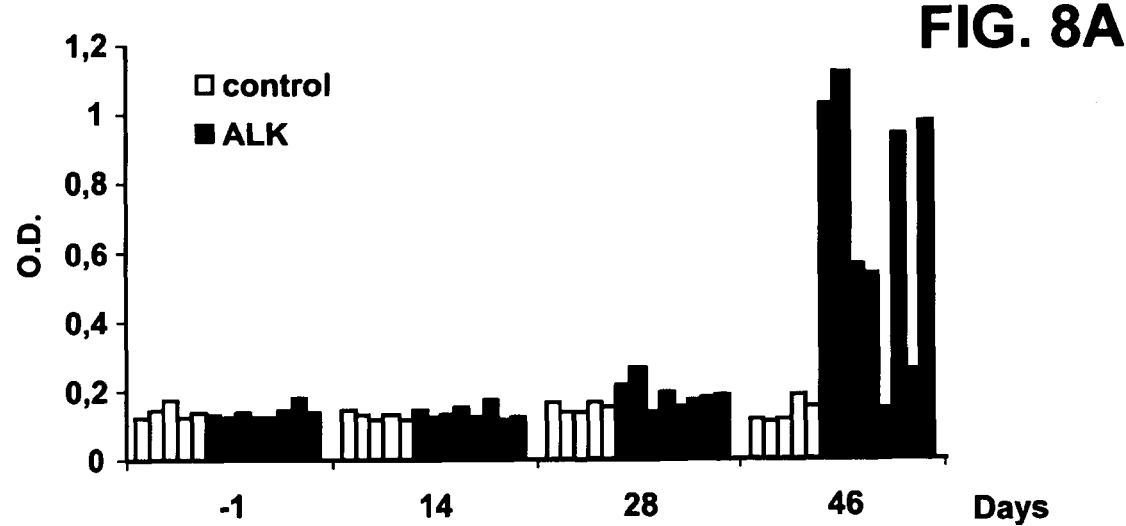
FIG. 8. Vaccination with ALK peptide elicits a specific antibody response but does not protect mice against lymphoma growth. (a) BALB/c mice were vaccinated with purified GST-ALK-KHL as described in the Methods section. Specific anti-ALK immunoglobulins were measured by ELISA on the indicated days. (b) Vaccinated mice were challenged after vaccination with 1×10⁶ NPM-ALK expressing lymphoma cells s.c. Tumor growth was measured over time. Bars represent standard errors.
Figure 8B:
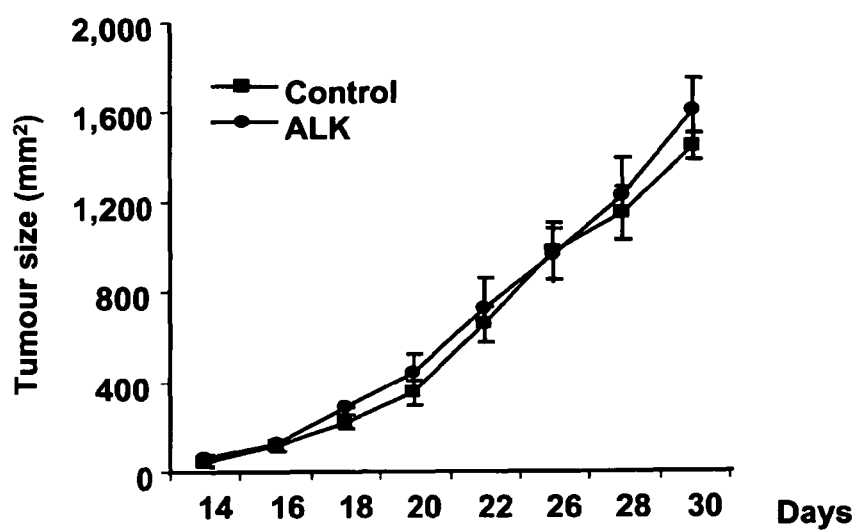

To further elucidate the immunological mechanisms necessary for lymphoma protection in the present model, three BALB/c knock-out mouse models, lacking either B cells (Ig μ-chain −/−), IFNγ (IFNγ −/−), or perforin (perforin −/−) mediated responses were employed. Mice were vaccinated twice and then challenged with lymphoma cells s.c., and tumor growth was measured over time. Mice lacking the B lymphocytes (Ig μ-chain −/−) were successfully protected by ALK vaccination and showed an in vivo cytotoxic activity comparable to wild type mice (FIGS. 4a,b). Notably, wild type mice vaccinated with the ALK plasmid displayed very low titers of anti-ALK antibodies and vaccinations with purified ALK peptides in combination with GM-CSF stimulated a strong antibody responses with high titers of anti-ALK antibodies but lack detectable anti-tumor responses (FIG. 8). Altogether, these data indicate that B cells or antibody production are dispensable to obtain a significant protection against ALK lymphomas in the present model. These results differ from those obtained with other Tg mice models (such as HER-2 transgenic BALB/c mice) in which antibodies against the extracytoplasmic portion of the oncogenic tyrosine kinase are essential to obtain a significant protection.

In the absence of IFNγ, ALK vaccinated mice were not protected and in perforin −/− mice an intermediate protection and cytotoxic activity, as compared to immunocompetent animals, was found (FIGS. 4a,b), indicating that anti-ALK cytotoxic activity requires IFNγ production and, to a lesser extent, perforin but could be mediated by other effector molecules.

Finally, the role of CD4 and CD8 cells was established after depletion with specific anti-CD4 or anti-CD8 antibodies. First, mice were vaccinated and then selectively depleted for CD4 or CD8 T cells before the tumor challenge. The loss of CD4 T cells did not significantly alter the tumor protection after vaccination, meanwhile lymphoma cells grew in a comparable rate to controls in the absence of CD8 cells (FIG. 4c). Moreover, the xenograft tumor growth of vaccinate mice, after depletion of Natural Killer (NK) cells (<5% NK) with rabbit anti-asialo antibodies, was statistically similar to control animals. In addition, NK depleted mice display an efficient and specific cytotoxic response against ALK positive cells in vivo. In summary, these findings demonstrated that ALK vaccination protects mice from lymphoma growth mainly via T-cell-mediate responses, and requires cytotoxic T-cells, as effectors.

Although ALK fusion proteins are expressed in only 2-3% of NHL, the present disclosure demonstrates that ALK is endowed with many of the features of a perfect tumor vaccination antigen, i.e. specificity, strong immunogenicity, and absolute requirement for tumor maintenance. In fact, the physiological expression of ALK is almost completely restricted to the fetal life, whereas in adult mammals it is detected at high levels only in rare neurons within the central nervous system and in the spinal cord. Since these compartments represent immunological sanctuaries, littler if any, autoimmune or severe/adverse reactions should be expected after ALK vaccination. This hypothesis is supported by the present findings, which demonstrated that mice vaccinated with human ALK were perfectly healthy, fertile and did not display noticeable signs or symptoms (up to 18 months of follow-up), although they developed specific lymphocytes against the murine ALK in the absence of detectable histological signs of acute and/or chronic inflammation. Moreover, the pathological expression of human ALK can elicit measurable B- and T-cell responses in patients with ALCL lymphoma without concomitant autoimmune and/or neurological disorders. The sustained signaling of ALK fusion proteins for the maintenance of the ALCL phenotype and survival is well established. This evidence provides a strong rational and a significant advantage in the design of ALK-based vaccines, since the selection and/or the escape of an ALCL neoplastic clone lacking ALK might be very unlikely.

Finally, but not less importantly, ALK lymphomas represent the most common high-grade lymphoma in children. In these patients, a long-term immuno-surveillance induced by an ALK vaccination could be decisive in preventing lymphoma recurrence as well as in assuring a long lasting remission or, in the best of cases, the complete eradication of the disease, which might be achieved by targeting ALK translocated tumor stem cells.

The present data are also in line with previous findings, which demonstrated the absolute need to decrease the tumor burden to have successful vaccination strategies and to reach curative disease-free survival rates or cures. Today, high dose and/or poly-chemotherapeutic approaches are commonly used, however, these approaches are associated with serious constrains including high toxicity, and increased risk of secondary drug-induced neoplasms. These undesired side effects are of particular relevance in young patients. Thus, alternative protocols taking advantage of more specific compounds (kinase inhibitors), less toxic regiments (i.e. chemoprevention protocols, tailored schedules etc.) capable to better preserve the host immunity, or chemotherapeutic compounds favoring necrosis versus apoptosis (which should enhance tumor antigen presentation) should be consider in association with the vaccine protocols. Our data support this avenue and provide the scientific rational for future clinical applications.

The protocols of ALK DNA vaccination used in the present mouse model will be adapted for clinical application in human patients.

ALK DNA vaccination protocols will be designed following the guidelines established for other antigens in human patients, such as in prostate cancer (Miller et A. M. et al. *J. Immunother.* 28, 389-95 (2005); Roos A. K. et al. *Methods Mol Biol.* 423, 463-72 (2008)). As a starting protocol three different amounts of ALK DNA are used: 100 μg (90 μg intramuscularly [IM]+10 μg intradermally [ID]), 300 μg (270 μg IM+30 μg ID), and 900 μg (810 μg IM+90 μg ID). To optimize vaccination, the following cytokines will be given concomitantly as vaccine adjuvants: GM-CSF (molgramostim, Leucomax, Schering-Plough & Novartis, Sweden) (40 μg/day for 3 days starting 2 days before vaccination) subcutaneously (SC) at the same site as vaccination and IL-2 (aldesleukin, Proleukin, Chiron, Holland) (75 μg/day for 7 days starting the day after vaccination) SC in the same extremity.

Successive modifications and adaptations will be pursued based on the immunological responses of the patients.

Materials and Methods

Plasmids, Cells Lines and Reagents.

The majority of the cytoplasmic domain of ALK (SEQ ID No.:1), that is translocated in NPM-ALK fusion protein, was cloned into the pDEST vector (Invitrogen) to obtain the pDEST-ALK construct. The fragment from bp 469 to 1372 of the NPM-ALK cDNA was cloned into the pDEST vector to obtain pDEST-ALKt, which contains a truncated form of ALK lacking part of the tyrosine kinase domain (SEQ ID No.: 2). The pDEST-ALK$^{K210R}$ plasmid (SEQ ID No.:3) was obtained by site-directed mutagenesis as described in Chiarle R. et al. *Nat Med* 11, 623-629 (2005).

The two cells lines used in this study (ALK-OVA and VAC) were immortalized from primary lymphomas derived from NPM-ALK Tg mice (Chiarle R. et al. *Blood* 101, 1919-1927 (2003)) backcrossed on the BALB/c background. Doxorubicin was purchased at 2 mg/ml concentration from Pharmacia (Milan Italy)

Mice, In Vivo Cell Depletion and Tumor Challenge.

BALB/c mice were from Charles River Laboratories Italia S.p.A. Mice knock out (KO) for the Ig μ heavy-chain gene (BALB-Igμ chain −/−; Qin Z. et al. *Nat Med* 4, 627-630 (19938)) were kindly provided by Thomas Blankenstein (Freie University, Berlin, Germany). The IFNγ gene KO mice (BALB-IFNγ −/−; Clynes R. et al. *Proc Natl Acad Sci USA* 95, 652-656 (1998)) were from Jackson Laboratories (Bar Harbor, Me., USA). Mice KO for the perforin gene (BALB-perforin −/−; Smyth M J et al. *J Immunol.* 162, 6658-6662 (1999)) were from the Peter MacCallum Cancer Institute (East Melbourne, Australia). Mice were treated properly and ethically in accordance with European Community guidelines.

When required, on day −15 and −14 days before tumor challenge mice received two intravenous injections of 0.2 ml PBS containing 40 µg of anti-CD8 (Lyt 2, purified Ab, CL168AP Cederlane Laboratories, Canada) or 40 µl of anti-CD4 (L3T4 ascite, CL012A Cederlane Laboratories, Canada) or anti-asialo Ab (Rabbit anti-asialo GM1, 986-10001, Cedarlane Laboratories, Canada). Flow cytometry of residual blood CD4 and CD8 T-cells and Natural Killer cells, collected 7 days after the last injection, showed that targeted cells were selectively decreased below 1% of cells.

Mice were challenged subcutaneously in the right flank with 0.2 ml PBS of a single suspension containing $10^5$ to $10^6$ ALK-OVA and VAC lymphoid cells, as indicated in each experiment. The cages were coded, and the incidence and the growth of tumors were evaluated at the indicated times in a blind fashion. Neoplastic masses were measured with calipers in the two perpendicular diameters.

Vaccinations.

For DNA electroporation, 50 µg of pDEST empty vector or pDEST-ALK (ALK) vector in 20 µl of 0.9% NaCl with 6 mg/ml polyglutamate were injected on days 0 and 7 into both the tibial muscle of anesthetized BALB/c mice. An additional group of mice was vaccinated with the pDEST-ALK plasmid combined with the same amount of a pcDNA3 plasmid coding for GM-CSF (SEQ ID No.:4). Electric pulses were applied by two electrodes placed on the skin and two square-wave 25 ms, 375 V/cm pulses were generated by a T820 electroporator (BTX, San Diego, Calif.). On day 14 and 7 months after the second vaccination mice were challenged with $1\times10^6$ NPM-ALK expressing lymphoma cells derived from NPM-ALK BALB/c Tg mice injected subcutaneously (s.c) in the right flank. Protection was evaluated as the percentage of lymphoma-free mice 21 days after challenge.

For peptide vaccination, mice were vaccinated with 50 µg of purified GST-ALK (coding for the entire cytoplasmic domain of the ALK protein—SEQ ID No.:5) conjugated with KLH (Keyhole Limpet Hemocyanin) in combination with 10.000 U of recombinant GM-CSF (SEQ ID No.:6) on days 0, 15 and 29. To measure specific anti-ALK immunoglobulin production, ELISA plates were coated with purified GST-ALK protein.

Chemotherapy Protocols.

A single dose chemotherapy protocols was employed using doxorubicin (10 mg/kg) 7 day prior the i.v. injection of a challenging dose ($1\times10^6$) of NPM-ALK positive lymphoma cells. On days 14, 21 and 28 mice were then DNA vaccinated with empty (mock) or ALK-expressing plasmids (full arrows), as described above. Anti-ALK responses after chemotherapy were also studied in BALB/c mice, after a single i.v. injection with 10 mg/kg doxorubicin (day 0), followed by DNA vaccination (on days 7, 14 and 21), and then after 60 days by the s.c. injection of $1\times10^6$ NPM-ALK expressing lymphoma cells. Finally, to assess the utility of a combination chemotherapy approach, syngeneic mice (BALB/c and C57BL/6) were challenged with NPM-ALK positive lymphoma cells. Mice bearing approx 2 cm tumor masses (in the largest diameter) were then first treated for 12 consecutive days with 30 or 100 mg/day bid CEP-26939 (Cephalon, USA) followed by DNA vaccination. Tumor growth and overall survival were determined, overtime.

Histology and Immunohistochemistry.

For histological evaluation, tissue samples were fixed in 10% neutral buffered formalin, embedded in paraffin, sectioned at 4 µm, and stained with hematoxylin and eosin. For immunohistochemistry, formalin-fixed, paraffin embedded section were incubated with anti ALK antibody (Rabbit anti-ALK, Invitrogen, Carlsbad, Calif., USA, 1:1000). After washing, sections were overlaid with biotinylated goat anti-rabbit secondary antibody and revealed with the DAKO EnVision™+ System (Dako, Glostrup, Denmark).

In Vivo Cytotoxicity Assays.

BALB/c mice were vaccinated twice with the indicated plasmids and 7 days after the second vaccination they were i.v. injected with $10^7$ wild type splenocytes mixed with $10^7$ NPM-ALK Tg BALB/c splenocytes labelled with different amounts of CFSE (0.5 µM and 5 µM, respectively). After 72 hours, mice were sacrificed and splenocytes were stained with CD4-APC antibody (Pharmingen) and analysed by flow cytometry. Percentages of ALK-directed specific cytotoxicity were calculated by normalizing the numbers of residual NPM-ALK expressing CD4 T-cells (CSFE high) with the total amount of CD4+CSFE+ T-cells in mock and ALK vaccinated mice.

Elispot Assay.

ELISPOT assay was done using the murine IFNγ Elispot kit (Becton-Dickinson) according to the manufacture's instruction. Briefly, splenocytes ($1\times10^6$) from non-immunized and immunized mice were incubated in triplicates in 96-well plates (Millipore) for 18 hours at 37° C. alone or together with NPM-ALK Tg BALB/c splenocytes or recombinant GST-mALK protein obtained from a vector in which the cytoplasmic portion of murine ALK (mALK) was cloned in frame with GST. Spot were scanned with ImmunoSpot series 3A Analyzer and counted using the ImmunoSpot image analyzer software v3.2 (CTL ImmunoSpot, Cleveland Ohio). Results are expressed as spot forming units (SFU)/$1\times106$ cells.

Statistical Analyses.

A two sample t test was used for statistical analysis of the tumor growth and cytotoxicity. Significant differences in survival of mice with Kaplan-Meier analysis were determined. P values less than 0.05 were considered significant.

Genebank References.

Human ALK: NM_004304.3. and NP_004295.2. Murine ALK: NM007439, NC_000083.5 and MGI: 103305

Naturally, while the principle of the invention remains the same, the details of construction and the embodiments may widely vary with respect to what has been described and illustrated purely by way of example, without departing from the scope of the present invention.

The invention claimed is:

1. A method of treating or delaying the growth of an Anaplastic Lymphoma Kinase (ALK) protein expressing tumor comprising administering to a subject in need thereof a purified nucleic acid molecule comprising,
   i) a nucleotide sequence selected from the group consisting of the nucleotide of SEQ ID No.:2 encoding the intracytoplasmatic domain of an ALK protein lacking a tyrosine kinase domain and the nucleotide of SEQ ID NO.: 3, encoding the intracytoplasmatic domain of an ALK protein comprising an inactivating mutation in the catalytic domain; or
   ii) a nucleic acid sequence encoding the amino acid of SEQ ID NO.: 5, which is the intracytoplasmic domain of an ALK protein;
   wherein said purified nucleic acid molecule is administered in a therapeutically effective amount to treat or delay tumor growth.

2. The method according to claim 1, wherein the nucleic acid molecule is administered in combination with a nucleic acid molecule encoding Granulocyte-Monocytes Colony Stimulating Factor (GM-CSF).

3. The method according to claim 1, wherein the amino acid sequence of said intracytoplasmatic domain of said ALK protein is the amino acid sequence of the intracytoplasmatic domain of human ALK protein.

4. The method according to claim 1, wherein the tumor is a neuroblastoma, a glioblastoma, a soft tissue tumor, an ALK expressing lymphoma, an ALK expressing lung, breast, colon or prostate carcinoma.

5. The method according to claim 1, wherein the nucleic acid molecule is present in a plasmid.

\* \* \* \* \*